US011534471B2

(12) United States Patent
Ngwa

(10) Patent No.: US 11,534,471 B2
(45) Date of Patent: Dec. 27, 2022

(54) ISOLATION, PRESERVATION, COMPOSITIONS AND USES OF EXTRACTS FROM JUSTICIA PLANTS

(71) Applicants: DANA-FARBER CANCER INSTITUTE, INC., Boston, MA (US); THE BRIGHAM AND WOMEN'S HOSPITAL, INC., Boston, MA (US)

(72) Inventor: Wilfred F. Ngwa, Orlando, FL (US)

(73) Assignees: DANA-FARBER CANCER INSTITUTE, INC., Boston, MA (US); THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 16/649,015

(22) PCT Filed: Sep. 21, 2018

(86) PCT No.: PCT/US2018/052266
§ 371 (c)(1),
(2) Date: Mar. 19, 2020

(87) PCT Pub. No.: WO2019/060759
PCT Pub. Date: Mar. 28, 2019

(65) Prior Publication Data
US 2020/0289596 A1  Sep. 17, 2020

Related U.S. Application Data

(60) Provisional application No. 62/561,492, filed on Sep. 21, 2017.

(51) Int. Cl.
| | | |
|---|---|---|
| A61K 36/19 | (2006.01) | |
| A23L 5/20 | (2016.01) | |
| A23L 33/105 | (2016.01) | |
| A23L 5/30 | (2016.01) | |
| A61P 35/00 | (2006.01) | |
| A23J 3/18 | (2006.01) | |
| A23J 3/22 | (2006.01) | |
| A61K 9/19 | (2006.01) | |
| A61K 38/16 | (2006.01) | |
| A61K 47/42 | (2017.01) | |

(52) U.S. Cl.
CPC ............ *A61K 36/19* (2013.01); *A23J 3/18* (2013.01); *A23J 3/227* (2013.01); *A23L 5/23* (2016.08); *A23L 5/30* (2016.08); *A23L 33/105* (2016.08); *A61K 9/19* (2013.01); *A61K 38/168* (2013.01); *A61K 47/42* (2013.01); *A61P 35/00* (2018.01); *A23V 2002/00* (2013.01); *A61K 2236/37* (2013.01)

(58) Field of Classification Search
None
See application file for complete search history.

(56) References Cited

U.S. PATENT DOCUMENTS

| | | | |
|---|---|---|---|
| 19,775 | A | 3/1858 | Hedenberg |
| 5,959,185 | A | 9/1999 | Streit et al. |
| 5,973,234 | A | 10/1999 | Mueller et al. |
| 5,977,445 | A | 11/1999 | Soper et al. |
| 5,994,075 | A | 11/1999 | Goodfellow |
| 6,344,600 | B1 | 2/2002 | Merot et al. |
| 6,365,411 | B1 | 4/2002 | Subbiah et al. |
| 7,005,146 | B2 | 2/2006 | Lee |
| 8,586,363 | B2 | 11/2013 | Voytas et al. |
| 8,697,359 | B1 | 4/2014 | Zhang |
| 8,715,748 | B2 | 5/2014 | Lowe et al. |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 8,999,641 | B2 | 4/2015 | Zhang et al. |
| 9,011,949 | B2 | 4/2015 | Brown et al. |
| 9,145,565 | B2 | 9/2015 | Carroll et al. |
| 9,181,535 | B2 | 11/2015 | Liu et al. |
| 9,700,067 | B2 | 7/2017 | Fraser et al. |
| 9,737,875 | B2 | 8/2017 | Brown et al. |
| 9,808,029 | B2 | 11/2017 | Fraser et al. |

(Continued)

FOREIGN PATENT DOCUMENTS

| | | |
|---|---|---|
| WO | 2003/055558 | 7/2003 |
| WO | 2005/048692 | 6/2005 |

(Continued)

OTHER PUBLICATIONS

Onyeabo (Acta Sci. Pol. Technol. Aliment. (2017), vol. 16, No. 2, pp. 217-230).*
Allard R.W., 1960, Principles of Plant Breeding, John Wiley and Son, pp. 115-161.
Andersson, C. R., et al. "A new hemoglobin gene from soybean: a role for hemoglobin in all plants." Proceedings of the National Academy of Sciences 93.12 (1996): 5682-5687.
Appleby, Cyril A., John D. Tjepkema, and Michael J. Trinick. "Hemoglobin in a nonleguminous plant, Parasponia: possible genetic origin and function in nitrogen fixation." Science 220.4600 (1983): 951-953.
Austin, Daniel F. Florida ethnobotany. CRC Press, 2004, Contents section.

(Continued)

*Primary Examiner* — Susan Hoffman
(74) *Attorney, Agent, or Firm* — Baker Donelson

(57) ABSTRACT

The present disclosure relates to the isolation, preservation, compositions and uses of extracts from a newly discovered species of *Justicia* plants. The present disclosure also relates to compositions comprising the extracts of the new species of *Justicia* plant, as well as methods of producing and using such compositions for treating blood disorders and/or for other health, food and industrial uses.

9 Claims, 12 Drawing Sheets

(56) References Cited

U.S. PATENT DOCUMENTS

| | | | |
|---|---|---|---|
| 9,826,772 | B2 | 11/2017 | Fraser et al. |
| 9,833,768 | B2 | 12/2017 | Brown et al. |
| 9,938,327 | B2 | 4/2018 | Shankar et al. |
| 9,943,096 | B2 | 4/2018 | Fraser et al. |
| 10,039,306 | B2 | 8/2018 | Vrljic et al. |
| 10,064,800 | B2 | 9/2018 | Ishikawa et al. |
| 10,195,136 | B2 | 2/2019 | Leeson et al. |
| 2004/0053236 | A1 | 3/2004 | McCallum et al. |
| 2007/0196526 | A1 | 8/2007 | Horska |
| 2008/0095913 | A1 | 4/2008 | Jones et al. |
| 2008/0107774 | A1 | 5/2008 | Jones et al. |
| 2010/0323041 | A1 | 12/2010 | Cyr |
| 2014/0295049 | A1 | 10/2014 | Ragot et al. |
| 2014/0357584 | A1 | 12/2014 | Zhang et al. |

FOREIGN PATENT DOCUMENTS

| | | |
|---|---|---|
| WO | 2005/055704 | 6/2005 |
| WO | 2007/048356 | 5/2007 |
| WO | 2013/019662 | 2/2013 |
| WO | 2013/028266 | 2/2013 |
| WO | 2013/031403 | 3/2013 |
| WO | 2014/034802 | 3/2014 |
| WO | 2016/060525 | 4/2016 |
| WO | 2019/060788 | 3/2019 |

OTHER PUBLICATIONS

Bogusz, Didier, et al. "Functioning haemoglobin genes in non-nodulating plants." Nature 331.6152 (1988): 178-180.

Briggs, Fred N. "Breeding Wheats resistant to bunt by the backcross method." Journal of the American Society of Agronomy 22.3 (1930).

Comai, Luca, et al. "Efficient discovery of DNA polymorphisms in natural populations by Ecotilling." The Plant Journal 37.5 (2004): 778-786.

Corrêa, Geone M., and Antônio F. de C. Alcântara. "Chemical constituents and biological activities of species of Justicia: a review." Revista Brasileira de farmacognosia 22.1 (2012): 220-238.

Dirr, Michael A. The reference manual of woody plant propagation: from seed to tissue culture; a practical working guide to the propagation of over 1100 species, varieties and cultivars No. 04; SB123 6, D5.. 1987.

Dorling, Kindersley. "Rhs AZ Encyclopedia of garden plants." United Kingdom 1136 (2008), Contents section.

El-Hennawy, M. A., et al. "Production of doubled haploid wheat lines (*Triticum aestivum* L.) using anther culture technique." Annals of Agricultural Sciences 56.2 (2011): 63-72.

Fehr, W. R. "Principles of cultivar development: development of hybrid cultivars." (1993), Macmillian Publishing Co. : USA.

Fernandez-Pomares et al., "Antiproliferative Activity of the Polar Extract of Justicia Spicigera on LNCaP Cells", Cancer Prevention Research, vol. 3, No. 12 2010.

França LT, Carrilho E, Kist TB. A review of DNA sequencing techniques. Q Rev Biophys. May 2002;35(2):169-200.

Gao F, Shen XZ, Jiang F, Wu Y, Han C. Retraction: DNA-guided genome editing using the Natronobacterium gregoryi Argonaute. Nat Biotechnol Aug. 8, 2017;35(8):797.

Garvin, M. R., and A. J. Gharrett. "DEco-Tilling: an inexpensive method for single nucleotide polymorphism discovery that reduces ascertainment bias." Molecular ecology notes 7.5 (2007): 735-746.

Gayatri, M. C., and R. Kavyashree. Plant Tissue Culture: Protocols in Plant Biotechnology. Alpha Science International, 2015, Contents section.

Gilchrist, Erin J., et al. "Use of Ecotilling as an efficient SNP discovery tool to survey genetic variation in wild populations of Populus trichocarpa." Molecular ecology 15.5 (2006): 1367-1378.

Gupta, Kapuganti J., et al. "Plant hemoglobins: important players at the crossroads between oxygen and nitric oxide." FEBS letters 585.24 (2011): 3843-3849.

Gur, Amit, and Dani Zamir. "Unused natural variation can lift yield barriers in plant breeding." PLoS Biol 2.10 (2004): e245.

Hallauer, A. R., and J. B. Miranda. "Quantitative genetics in maize breeding. Iowa State Univ. Press, Ames, Iowa." Quantitative genetics in maize breeding. Iowa State Univ. Press, Ames, Iowa. (1981), Contents section.

Hallauer, A. R., Wilbert A. Russell, and K. R. Lamkey. "Corn breeding." Corn and corn improvement 18 (1988): 463-564.

Harrington, James M., et al. "Analysis of human serum and whole blood for mineral content by ICP-MS and ICP-OES: development of a mineralomics method." Biological trace element research 160.1 (2014): 132-142.

Hiruma, Yuko, et al. "Increased signaling through p62 in the marrow microenvironment increases myeloma cell growth and osteoclast formation." Blood, The Journal of the American Society of Hematology 113.20 (2009): 4894-4902.

Hoy, Julie A., and Mark S. Hargrove. "The structure and function of plant hemoglobins." Plant Physiology and Biochemistry 46.3 (2008): 371-379.

Jensen, Neal F. Plant breeding methodology. John Wiley & Sons, Inc., 1988 Contents section.

Jokipii-Lukkari, Soile, et al. "Intrinsic non-symbiotic and truncated haemoglobins and heterologous Vitreoscilla haemoglobin expression in plants." Journal of experimental botany 60.2 (2009): 409-422.

Kakar, Smita, et al. "Structure and reactivity of hexacoordinate hemoglobins." Biophysical chemistry 152.1-3 (2010): 1-14.

Keating, Brian R., and Kim Long. How to Make Tea: The Science Behind the Leaf. Ivy Press, 2015, Contents section.

Kress WJ, Erickson DL, Swenson NG, Thompson J, Uriarte M, Zimmerman JK. Advances in the use of DNA barcodes to build a community phylogeny for tropical trees in a Puerto Rican forest dynamics plot. PLoS One. Nov. 9, 2010;5(11): e15409.

Kress, W. John, and David L. Erickson. "DNA barcodes: methods and protocols." DNA Barcodes. Humana Press, Totowa, NJ, 2012. 3-8.

Kress, W. John, et al. "Plant DNA barcodes and a community phylogeny of a tropical forest dynamics plot in Panama." Proceedings of the National Academy of Sciences 106.44 (2009): 18621-18626.

Liu, Lin, et al. "Comparison of next-generation sequencing systems." Journal of Biomedicine and Biotechnology 2012.

Lusser, Maria, et al. New plant breeding techniques: state-of-the-art and prospects for commercial development. Luxembourg: Publications Office of the European Union, 2011. Joint Research Center (JRC) Institute for Prospective Technological Studies of the European Commission, 2011, "New plant breeding techniques—State-of-the-art and prospects for commercial development.".

Maluszynski, M., et al., eds. Doubled haploid production in crop plants: a manual. Springer Science & Business Media, 2003.

Mardis ER. Next-generation DNA sequencing methods. Annu Rev Genomics Hum Genet. 2008;9:387-402.

Mejlhede, N., et al. "EcoTilling for the identification of allelic variation in the powdery mildew resistance genes mlo and Mia of barley." Plant breeding 125.5 (2006): 461-467.

Meksem, Khalid, and Gunter Kahl, eds. The handbook of plant genome mapping: genetic and physical mapping. John Wiley & Sons, 2006, Contents section.

Michelmore, Richard W., I. Paran, and R. V. Kesseli. "Identification of markers linked to disease-resistance genes by bulked segregant analysis: a rapid method to detect markers in specific genomic regions by using segregating populations." Proceedings of the national academy of sciences 88.21 (1991): 9828-9832.

Mpiana Pius et al: In vitro effects of anthocyanin extracts from Justicia secunda Vahl on the solubility of haemoglobin S and membrane stability of sickle erythrocytes. Blood Transfusion Oct. 2010. Vol. 8, No. 4, pp. 248-254.

Munshi, Anupama, Marvette Hobbs, and Raymond E. Meyn. "Clonogenic cell survival assay." Chemosensitivity. Humana Press, 2005. 21-28.

Nath, Karl A., et al. "Age sensitizes the kidney to heme protein-induced acute kidney injury." American Journal of Physiology-Renal Physiology 304.3 (2013): F317-F325.

(56) References Cited

OTHER PUBLICATIONS

National Cancer Institute Comprehensive Cancer Information https://www.cancer.gov/, accessed Jun. 14, 2021.
Nieto, Cristina, et al. "EcoTilling for the identification of allelic variants of melon eIF4E, a factor that controls virus susceptibility." BMC plant biology 7.1 (2007): 1-9.
Paterson, 1996, Genome Mapping in Plants. R.G. Landes, Austin, Contents section.
Physiology, Edited by Edward E. Selkurt, 1963, J & A Churchill, Ltd: London, Contents section.
Pierik, Rudolf Leonardos Maria. In vitro culture of higher plants. Springer science & business media, 1997.
Podar, K., D. Chauhan, and K. C. Anderson. "Bone marrow microenvironment and the identification of new targets for myeloma therapy." Leukemia 23.1 (2009): 10-24.
Quarrie, Steve A., et al. "Bulk segregant analysis with molecular markers and its use for improving drought resistance in maize." Journal of experimental botany 50.337 (1999): 1299-1306.
Seymour DK, Filiault DL, Henry IM, Monson-Miller J, Ravi M, Pang A, Comai L, Chan SW, Maloof JN. Rapid creation of Arabidopsis doubled haploid lines for quantitative trait locus mapping. Proc Natl Acad Sci USA. Mar. 13, 2012;109 (11):4227-32.
Simmonds, Norman Willison. "Principles of crop improvement." Principles of crop improvement. (1979).
Strader, Michael Brad, et al. "Oxidative instability of hemoglobin E ($\beta$26 Glu? Lys) is increased in the presence of free a subunits and reversed by a-hemoglobin stabilizing protein (AHSP): Relevance to HbE/$\beta$-thalassemia." Redox biology 8 (2016): 363-374.
Tanksley, S. D., and J. C. Nelson. "Advanced backcross QTL analysis: a method for the simultaneous discovery and transfer of valuable QTLs from unadapted germplasm into elite breeding lines." Theoretical and Applied Genetics 92.2 (1996): 191-203.
Zhang Z, Qiu F, Liu Y, Ma K, Li Z, Xu S. Chromosome elimination and in vivo haploid production induced by Stock 6-derived inducer line in maize (*Zea mays* L). Plant Cell Rep. Dec. 2008;27(12):1851-60.
W. R Fehr, 1987, Principles of Crop Development, Macmillan Publishing Co, Content and preface sections.
Watts, R. A., et al. "A hemoglobin from plants homologous to truncated hemoglobins of microorganisms." Proceedings of the National Academy of Sciences 98.18 (2001): 10119-10124.
Wright, Harold. "Commercial hybrid seed production." Hybridization of crop plants (1980): 161-176.
Sharma and Alam, Plant Tissue Culture, 2015, I.K. International Publishing House.

\* cited by examiner

FIGURE 2A
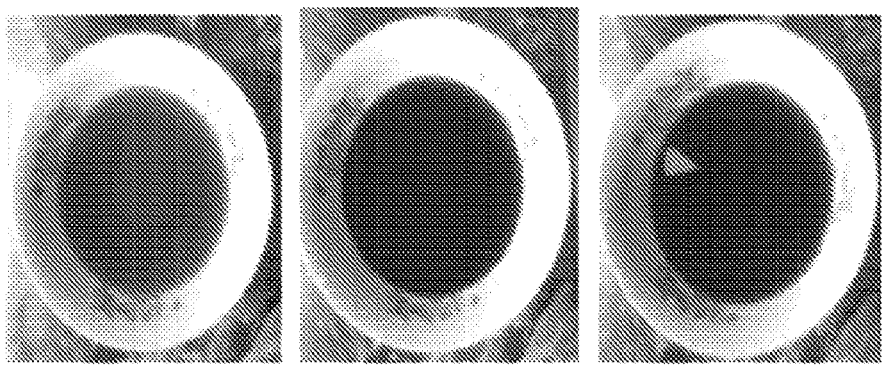
FIGURE 2B
| Samples | Hemoglobin (uM) | Hemoglobin (g/dl) |
|---|---|---|
| S1 - Light red | 28.07 | 0.044912 |
| S2 - Dark purple | 111.52 | 0.178432 |
| S3 - dark purple | 106.52 | 0.170432 |
| *S4 - Red* | *651.82* | *1.042912* |
| *S5 - Black* | *219.52* | *0.351232* |
| S6 - dry leaves | 103.27 | 0.165232 |
| S7 - dry stem | 15.07 | 0.024112 |
FIGURE 2C
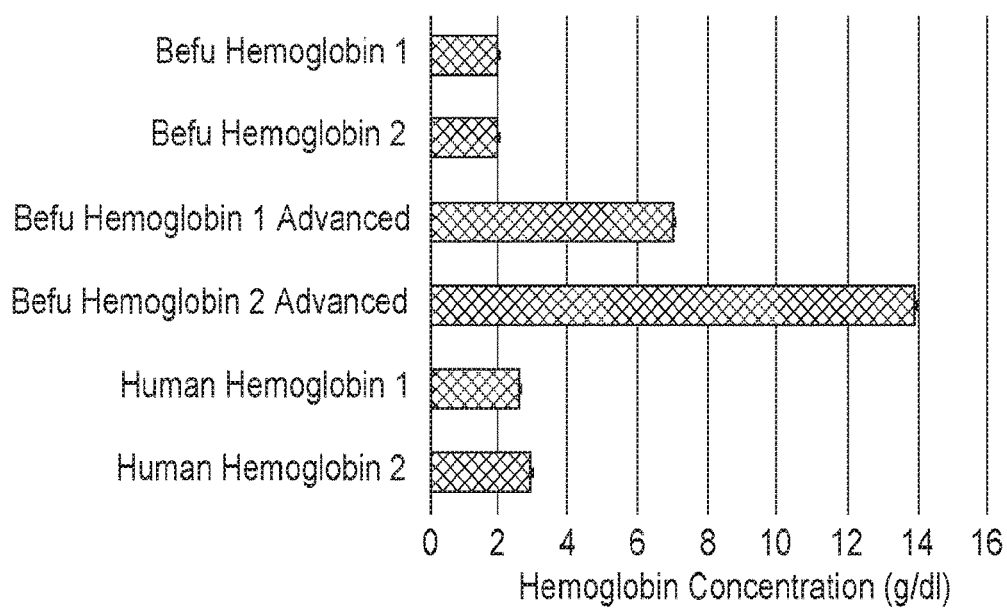

FIGURE 3

| Sample | Hemoglobin Concentration (g/dl) |
|---|---|
| Befu | 14 |
| Commercial hemoglobin same mass of lyophilized reconstituted | 3 |
| Beet root extract | 0 |
| Water | 0 |
| Acanthaceae plant from Puerto Rico | 0 |

FIGURE 8A
| Samples | Concentration (ug/gm) Test 1 | Concentration (ug/gm) Test 2 | Concentration (ug/gm) Average |
|---|---|---|---|
| Befu (Ly) | 60 | 70.18 | 65.09 |
| Befu (Px) | 39 | 44.89 | 41.95 |
FIGURE 8B
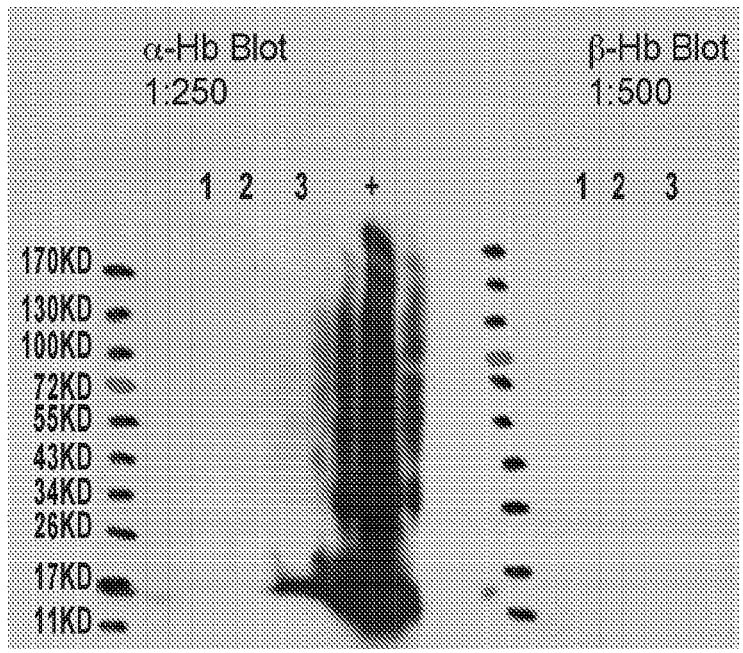
FIGURE 8C
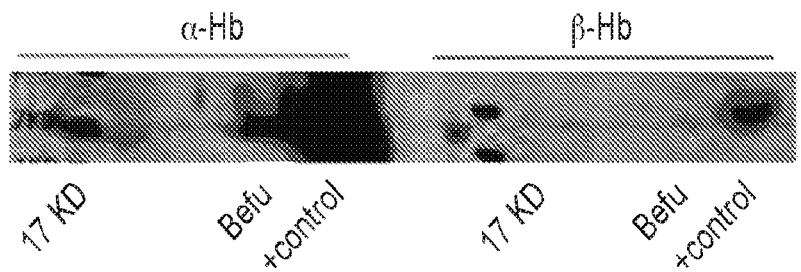

FIGURE 9A

| Befu extract | Human Blood |
|---|---|
| Analytes | |
| Ca | Ca |
| Sc | Li |
| Mn | Mn |
| Pb | Pb |
| Cr | Cr |
| Fe | Fe |
| V | I |
| Na | Na |
| Mg | Mg |
| Al | Al |
| Si | Si |
| P | P |
| K | K |
| Ti | Cu |
| | Cd |
| | Hg |
| | Ni |
| | O |
| | Sn |
| | Zn |

| Befu 15mg mass per ml | | Whole blood Final Concentration (ug/ml) from Harington et al. 2014 |
|---|---|---|
| Analyte | Final Concentration (ug/ml) from ICP-MS | |
| Na | 63.44 | 2275-2475 |
| Mg | 20.44 | 13-22 |
| Al | 1.12 | |
| Si | 1.94 | |
| P | 0.96 | |
| S | BDL | |
| Cl | BDL | |
| Ar | BDL | |
| K | 167.5 | 200 - 233 |
| Ca | 41.48 | 90.5 - 97.5 |
| Sc | BDL | |
| Ti | 0.02 | |
| V | BDL | |
| Cr | 0.1 | |
| Mn | 0.04 | |
| Fe | 2.64 | |
| Pb | 0.32 | |

FIGURE 9B

| Normal extract sample | |
|---|---|
| Analyte | Concentration (ug/ml) |
| Al | 1.14 |
| Ca | 41.48 |
| Cr | 1.12 |
| Fe | 2.64 |
| K | 167.5 |
| Mg | 20.44 |
| Mn | 0.14 |
| Na | 63.44 |
| P | 3.04 |
| Pb | 0.32 |
| Sc | 0.08 ☆ |
| Si | 1.94 |
| Ti | 0.06 ☆ |
| V | 0.04 ☆ |

ISOLATION, PRESERVATION, COMPOSITIONS AND USES OF EXTRACTS FROM JUSTICIA PLANTS

CROSS-REFERENCE TO RELATED APPLICATIONS

This application claims the benefit of priority to U.S. provisional application No. 62/561,492 filed on Sep. 21, 2017, which is hereby incorporated by reference in its entirety.

FIELD

The present disclosure relates to isolation, preservation, compositions and uses of extracts obtained from a distinct and new species of, *Justicia* plant. The present disclosure also relates to compositions of the extracts of the new species of *Justicia* plant, as well as methods of producing and making such compositions, for treating blood disorders, and/or using extract compositions for certain health, food and other benefits, and/or for industrial purposes, such as a natural coloring agent.

BACKGROUND

The following description includes information that may be useful in understanding the present disclosure. It is not an admission that any of the information provided herein is prior art or relevant to the presently claimed disclosures, or that any publication specifically or implicitly referenced is prior art.

*Justicia* is the largest genus of flowering plants in the family Acanthaceae. The *Justicia* genus has about 650 recognized species with hundreds of different plants possibly representing additional species. *Justicia* plants are typically found in pantropical and tropical climate areas. Plants of this genus are native in tropical to warm temperate regions, including Africa, the Americas, and India. Plants belonging to the *Justicia* genus are evergreen perennial plants. They are shrubs or subshrubs with strongly-veined leaves and lip-shaped corolla. For further information on this genus of plants, see, e.g., Austin, Daniel F. (2004), Florida Ethnobotany, CRC Press, p. 381, ISBN 978-0-8493-2332-4; and, RHS A-Z encyclopedia of garden plants, United Kingdom: Dorling Kindersley (2008), p. 1136, ISBN 1405332964.

Some *Justicia* species are cultivated for their ornamental value, while extracts of some species of *Justicia* are used for the medical needs such as treating skin conditions, HIV, asthma, allergies, migraines and the like.

However, there is a concern about the shortage of human blood that affects patients of all ages such cancer patients, surgical patients, patients in life-threatening emergency care, or military members. Blood transfusions and/or blood substitute supply can help many people in emergent situations who have lost a lot of blood by acute hemorrhage or during surgical operation, and also those needing long-term treatments, such as for cancer and blood diseases. Despite intense research effort directing to the development of an adequate blood substitute, to date there is rarely a substitute for human blood and blood products that can be easily stored and portable with application to potentially all blood types.

Thus, there is an unmet need in the art to identify and supply a safe plant-based blood substitute, which is able to save and sustain many precious lives. These safe components substituting human blood are needed for life-saving treatment and life-sustaining care to patients suffering from emergent blood shortage and/or blood-related diseases.

SUMMARY OF THE DISCLOSURE

The present disclosure provides a new *Justicia* plant species and its tissue extract composition rich in blood constituents, as well as methods of obtaining the extract composition from the plants.

Blood in humans and other animals delivers necessary substances such as nutrients and oxygen to the cells and transports metabolic waste products away from those same cells. Hemoglobin or haemoglobin, abbreviated Hb or Hgb, is the iron-containing oxygen-transport metalloprotein in the red blood cells of all vertebrates including human. One of critical roles of hemoglobin is to carry oxygen in blood.

Plants, like humans, have hemoglobin genes. However, the concentration of hemoglobin expressed in plant tissues is orders of magnitude lower than that in human blood.

The present disclosure provides a new *Justicia* plant comprising leaves with unusually high levels of hemoglobin and other blood components. Also, the present disclosure provides that lyophilized leaf extracts yield hemoglobin at levels comparable to those of the same mass of lyophilized human hemoglobin. In some embodiments, analyses described in the disclosure reveal that 'Befu' plant extracts have high levels of a-hemoglobin, b-hemoglobin, and many essential elements found in human blood. In some embodiments, a significant role for high concentrations of blood components in 'Befu' leaves is provided for applications in medicine such as treating blood disorder and various cancer, and in the food industry such as for use in food coloring.

The present disclosure provides lyophilized extracts isolated from a *Justicia sanguinis* plant or plant part thereof. In some embodiments such lyophilized extracts comprise hemoglobin.

The present disclosure provides compositions comprising hemoglobin isolated from a *Justicia sanguinis* plant or plant part thereof. In some embodiments, such compositions comprise α-hemoglobin and β-hemoglobin.

The present disclosure provides compositions comprising isolated hemoglobin which can be used as a blood substitute.

The present disclosure provides compositions comprising extracts from *Justicia* plants which are capable of treating a blood disorder, blood cancer and/or cancer. In some embodiments, the blood disorder being treated is anemia, hemophilia, and/or blood clots. In some embodiments, the blood cancer being treated is multiple myeloma, an acute leukemia, an advance phase chronic myelogenous leukemia (CML), a high risk myelodysplastic syndrome (MDS), an advanced myelofibrosis (MF), and/or a relapsed or refractory chronic lymphocytic leukemia (CLL).

The present disclosure provides methods of producing a lyophilized extract from a *Justicia sanguinis* plant or a plant part thereof, said method involving the steps of a) isolating an extract from the *Justicia sanguinis* plant or plant part thereof; b) centrifuging the isolated extract to produce a concentrated extract; and c) lyophilizing the concentrated extract to produce a lyophilized extract.

In some embodiments, there is provided a novel *Justicia* plant species, preliminarily designated herein as *Justicia sanguinis*. One representative genotype of this new plant species is designated 'Befu.' Tests are underway to confirm the initial *sanguinis* species designation of this new plant species discovered in a cultivated area and described herein. This disclosure thus relates to the *Justicia* plants as described herein, parts of the *Justicia* plants described herein, extracts of the *Justicia* plants described herein, and to plant cells of the *Justicia* plants described herein.

In some embodiments, the present disclosure teaches a method for treating prostate cancer, said method comprising administering an extract from a *Justicia sanguinis* plant to a patient in need thereof, thereby reducing the survival of prostate cancer cells in said patient; wherein a representative sample of seed or tissue culture of said *Justicia sanguinis* plant has been deposited under deposit ATCC Accession No. PTA-127079.

In some embodiments, the present disclosure teaches that the extracts of the present disclosure are produced by contacting the *Justicia sanguinis* plant or part thereof with a solvent, thereby creating an extraction solution; and recovering the liquid phase of the extraction solution, thereby producing the extract.

In some embodiments, the present disclosure teaches extracts wherein the solvent is water.

In some embodiments, the extracts of the presently disclosed methods use water at a temperature between about 60° F. and about 180° F. at the time that the solvent is contacted with the plant.

In some embodiments, the extracts of the presently disclosed methods utilize water that is maintained at a temperature between about 60° F. and about 180° F. until the liquid phase is recovered to produce the extract.

In some embodiments, the present disclosure teaches a method for reducing survival rate of prostate cancer cells in vitro, said method comprising contacting prostate cancer cells with an extract from a *Justicia sanguinis* plant, thereby reducing the survival rate of the prostate cancer cells compared with control prostate cancer cells that are not contacted with the extract; wherein a representative sample of seed or tissue culture of said *Justicia sanguinis* plant has been deposited under ATCC Accession deposit No. PTA-127079.

In some embodiments, the present disclosure teaches a method for producing a shelf-stable blood substitute, said method comprising the steps of: a) contacting a *Justicia sanguinis* plant or part thereof with a solvent; thereby creating an extraction solution, b) recovering the liquid phase of the extraction solution, and c) lyophilizing the liquid phase to produce a dry, shelf-stable blood substitute.

In some embodiments, the present disclosure teaches that the shelf-stable blood substitute retains at least 50% of its hemoglobin content for two weeks at room temperature.

In some embodiments, the present disclosure teaches that the shelf-stable blood substitute retains at least 60% of its hemoglobin content for two weeks at room temperature.

In some embodiments, the present disclosure teaches that the shelf-stable blood substitute retains at least 70% of its hemoglobin content for two weeks at room temperature.

In some embodiments, the present disclosure teaches that the shelf-stable blood substitute retains at least 80% of its hemoglobin content for two weeks at room temperature.

In some embodiments, the presently disclosed methods for producing a shelf-stable blood substitute utilize water at a temperature between about 60° F. and about 180° F. at the time that the water solvent is contacted with the plant.

In some embodiments, the presently disclosed methods for producing a shelf-stable blood substitute utilize water that is maintained at a temperature between about 60° F. and about 180° F. until the liquid phase is recovered from the extraction solution.

In some embodiments, the present disclosure teaches that the lyophilization of step c) occurs at −50° C. for 3 hours with a cooling rate of 1° C./minute; with primary drying at −50° C. for 60 hours at 3 Pa; and secondary drying at 0° C. for 4 hours and 20° C. for 8 hours at 3 Pa.

In some embodiments, the present disclosure teaches a method for producing a plant hemoglobin food additive, said method comprising the steps of: a) extracting plant hemoglobin by contacting a *Justicia sanguinis* plant or part thereof with a solvent; thereby creating an extraction solution, and b) recovering the liquid phase of the extraction solution, thereby producing the hemoglobin food additive.

In some embodiments, the present disclosure teaches that the food additive is added to a meat substitute food product comprising wheat gluten, such as those disclosed in U.S. Pat. Nos. 10,039,306, 9,943,096, 9,938,327, 9,833,768, 9,826,772, 9,808,029, 9,737,875, 9,700,067, and 9,011,949, each of which is hereby incorporated by reference in its entirety for all purposes.

In some embodiments, the present disclosure teaches that methods for producing compositions derived from extracts of *Justicia* plants (e.g. the food additive) comprising the step of c) concentrating the food additive through centrifugation and/or lyophilization.

In some embodiments, the present disclosure teaches methods wherein the food additive is centrifuged at a sufficient speed and time to produce a pellet comprising plant hemoglobin.

In some embodiments, the food additive is centrifuged between about 4,000 rpm and 16,000 rpm.

In some embodiments, the food additive is centrifuged for between 2 minutes, and 5 hours.

In some embodiments, the method of producing a food additive uses a *Justicia sanguinis* plants, wherein a representative sample of seed or tissue culture of said *Justicia sanguinis* plant has been deposited under ATCC Accession deposit No. PTA-127079.

IN some embodiments, the hemoglobin food additive is added to a primary flavor precursor compound selected from the group consisting of glucose, ribose, fructose, lactose, xylose, arabinose, glucose-6-phosphate, maltose, and galactose, and mixtures of two or more thereof and/or a secondary flavor precursor compound selected from the group consisting of cysteine, cystine, selenocysteine, thiamine, methionine, and mixtures of two or more thereof.

BRIEF DESCRIPTION OF THE DRAWINGS

FIG. 2A shows a picture of new safe 'Befu' extracts of different concentrations with methods that preserve the key components of blood such as Ca, Sc, Mn, Pb, Cr, Fe, V, Na, Mg, Al, Si, P, K, Ti, and Cr. FIG. 2B presents high level of hemoglobin following isolation and preservation of extract from 'Befu' plant. FIG. 2C shows comparison results of hemoglobin concentration and/or level. 3 mg/ml of lyophilized 'Befu' hemoglobin (Befu Hemoglobin 1 and 2 Advanced) has a significantly higher concentration of hemoglobin than that of same mass of human hemoglobin.

FIG. 3 demonstrates more comparison results of hemoglobin concentration from beet root extract, water, and Acanthaceae plant from Puerto Rico.

FIG. 8A shows results of ELISA analysis that verifies presence of human-type hemoglobin in 'Befu' extracts. FIGS. 8B and 8C provide Western Blot analysis results showing that 'Befu' extracts are strongly positive for human a-Hemoglobin (α globin) and weakly positive for human b-Hemoglobin β globin).

FIG. 9A shows levels of analytes from 'Befu' compared to whole human blood. Isolation and extraction process can allow for higher or lower concentrations of each analyte as may be needed for treating different blood disorders. The key components of blood are presented as detected analytes Ca, Sc, Mn, Pb, Cr, Fe, V, Na, Mg, Al, Si, P, K, Ti, and Cr. FIG. 9B shows essential mineral components of human blood found during ICP-MS analysis of 'Befu' leaf extract. Elements Sc, Ti and V, shown in dark gray (and starred) are not typical analytes in human blood. Remarkably, other blood components were also found in the 'Befu' extracts that can be useful for health and wellness applications.

FIG. 10A shows image of colonies in cell culture plates. FIG. 10B shows percent survival relative to controls. FIG. 10C shows result of blood urea nitrogen (BUN) levels in animals administered with the leaf extract relative to that of animals in a control cohort. A549=adenocarcinomic human alveolar basal epithelial cells; HUVECS=Human umbilical vein endothelial cells; PC3=human prostate cancer cells; RWPE=normal prostate epithelial cell line.

DETAILED DESCRIPTION

Figure 1A:
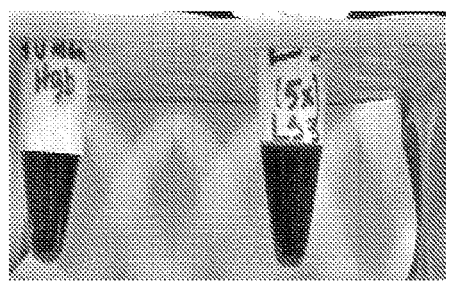
FIG. 1A provides a picture of commercial hemoglobin (Hgb) sample and lyophilized 'Befu' extracts (LS3) sample rapidly reconstituted in sterile water.

While the following terms are believed to be well understood by one of ordinary skill in the art, the following definitions are set forth to facilitate explanation of the presently disclosed subject matter. The following description includes information that may be useful in understanding the present disclosure. It is not an admission that any of the information provided herein is prior art or relevant to the presently claimed disclosures, or that any publication specifically or implicitly referenced is prior art.

According to the present disclosure, a new and distinct species of *Justicia* plant is identified and designated 'Befu' (Blood Extract for Universal). In some embodiments, leaves and stems of this 'Befu' plant are used to obtain extracts with high level of blood components such as hemoglobin and other constituents. In some embodiments, the 'Befu' tissue extracts can be preserved for a long period of time in a stable state and applied for treating diseases required for a supply of blood and/or blood-related diseases (e.g. blood disorders). In other embodiments, the 'Befu' tissue extracts can be modified for various applications in medicine and food industry. The present disclosure provides a potential candidate for blood substitute and use for treatment of blood disorders including: anemia, bleeding disorders such as hemophilia or trauma, blood clots, and blood cancers such as leukemia, lymphoma, and myeloma. In some embodiments, the isolated extract is safe with major advantages over other blood substitutes with development. In general, blood transfusion with other blood substitutes may causes allergic reactions, fever, acute immune hemolytic reaction, and blood-borne infections such as HIV, Hepatitis B and C, and West Nile Virus etc. In another embodiment, the 'Befu' tissue extracts having at least blood constituents is isolated and/or enriched with high levels of hemoglobin and blood analytes. Also, the present disclosure provides methods of isolating and extracting 'Befu' tissues, and applying and using the 'Befu' extracts as a superior safe blood substitute.

Definitions

In the description and tables that follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Blood substitute Blood substitute is intended to be a material having the ability to transport and supply oxygen to vital organs and tissues. Accordingly, the term encompasses materials and plant-based extracts containing blood constituents. The terms also carry with them the disclosure of an exemplary use of the composition and its formulation. For example, a "blood substitute" is of use to replace blood in the context of, e.g., trauma, stroke, ischemia/reperfusion injury, surgery, anemia or other injuries, insults and diseases in which a blood transfusion might be indicated. These terms, as used herein, also refer to Hb formulations capable of delivering oxygen or carbon monoxide to a tissue. These formulations are of use in injuries, insults and diseases characterized by the subject having adequate blood volume, yet the blood has inadequate ability to carry and/or deliver oxygen or carbon monoxide to tissues.

Essentially all the physiological and morphological characteristics. A plant having essentially all the physiological and morphological characteristics means a plant having the physiological and morphological characteristics of the recurrent parent, except for the characteristics derived from the converted gene.

Immunity to disease(s) and or insect(s). A *Justicia* plant which is not subject to attack or infection by specific disease(s) and or insect(s) is considered immune.

Intermediate resistance to disease(s) and or insect(s). A *Justicia* plant that restricts the growth and development of specific disease(s) and or insect(s), but may exhibit a greater range of symptoms or damage compared to resistant plants. Intermediate resistant plants will usually show less severe symptoms or damage than susceptible plant varieties when grown under similar environmental conditions and/or specific disease(s) and or insect(s) pressure, but may have heavy damage under heavy pressure. Intermediate resistant *Justicia* plants are not immune to the disease(s) and or insect(s).

Lyophilization. Lyophilization refers a process that is used to preserve materials and increase their shelf life, including biological materials, food, and pharmaceuticals. In general, lyophilization occurs by first freezing material to solidify it and then subjecting the material to a low pressure environment (below atmospheric pressure) to allow for sublimation of a component of the material. Typically the component is a liquid at standard temperature and pressure, one example being water. Depending on the type of material and volume being lyophilized, the process may take several days to complete.

Maturity (Date). Maturity refers to the stage when plants are of full size or optimum weight, and in marketable form or shape to be of commercial or economic value. In the region of best adaptability, maturity is the number of days from transplanting to optimal time for harvest.

New Breeding Techniques: New breeding techniques are said of various new technologies developed and/or used to create new characteristics in plants through genetic variation, the aim being targeted mutagenesis, targeted introduction of new genes or gene silencing (RdDM). Examples of such new breeding techniques are targeted sequence changes facilitated thru the use of Zinc finger nuclease (ZFN) technology (ZFN-1, ZFN-2 and ZFN-3, see U.S. Pat. No. 9,145,565, incorporated by reference in its entirety), Oligonucleotide directed mutagenesis (ODM), Cisgenesis and intragenesis, RNA-dependent DNA methylation (RdDM, which does not necessarily change nucleotide sequence but can change the biological activity of the sequence), Grafting (on GM rootstock), Reverse breeding, Agro-infiltration (agro-infiltration "sensu stricto", agro-inoculation, floral dip), Transcription Activator-Like Effector Nucleases (TALENs, see U.S. Pat. Nos. 8,586,363 and 9,181,535, incorporated by reference in their entireties), the CRISPR/Cas system (see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, which are all hereby incorporated by reference), engineered meganuclease re-engineered homing endonucleases, DNA guided genome editing (Gao et al., Nature Biotechnology (2016), doi: 10.1038/nbt.3547, incorporated by reference in its entirety), and Synthetic genomics. A complete description of each of these techniques can be found in the report made by the Joint Research Center (JRC) Institute for Prospective Technological Studies of the European Commission in 2011 and titled "New plant breeding techniques—State-of-the-art and prospects for commercial development", which is incorporated by reference in its entirety.

Plant adaptability. A plant having good plant adaptability means a plant that will perform well in different growing conditions and seasons.

Plant Cell. As used herein, the term "plant cell" includes plant cells whether isolated, in tissue culture or incorporated in a plant or plant part. In the present disclosure, this term refers to plant cells whether isolated in tissue culture or incorporated in a *Justicia* plant, a plant part thereof or an asexual clone thereof. Persons having skill in the art will appreciate that, unless otherwise noted, all references to a *Justicia* plant in the present disclosure can be read as referring to a plant cell from that plant. Therefore, embodiments described in the present disclosure which refer to a *Justicia* plant will also be understood to refer to a plant cell from said plant.

Plant Part. As used herein, the term "plant part" includes plant cells, plant protoplasts, plant cell tissue cultures from which *Justicia* plants can be regenerated, plant calli, plant clumps and plant cells that are intact in plants or parts of plants, such as embryos, pollen, ovules, flowers, seeds, rootstock, scions, stems, roots, anthers, pistils, root tips, leaves, meristematic cells, axillary buds, hypocotyls cotyledons, ovaries, seed coat endosperm and the like. In some embodiments, the plant part at least comprises at least one cell of said plant. In some embodiments, the plant part is further defined as a pollen, a meristem, a cell, or an ovule.

Quantitative Trait Loci (QTL) Quantitative trait loci refer to genetic loci that control to some degree numerically representable traits that are usually continuously distributed.

Regeneration. Regeneration refers to the development of a plant from tissue culture.

Resistance to disease(s) and or insect(s). A *Justicia* plant that restricts highly the growth and development of specific disease(s) and or insect(s) under normal disease(s) and or insect(s) attack pressure when compared to susceptible plants. These *Justicia* plants can exhibit some symptoms or damage under heavy disease(s) and or insect(s) pressure.

Rootstock. A rootstock is the lower part of a plant capable of receiving a scion in a grafting process.

Scion. A scion is the higher part of a plant capable of being grafted onto a rootstock in a grafting process.

Single gene converted (conversion). Single gene converted (conversion) plants refer to plants which are developed by a plant breeding technique called backcrossing wherein essentially all of the desired morphological and physiological characteristics of a plant are recovered in addition to the single gene transferred into the plant via the backcrossing technique or via genetic engineering. A single gene converted plant can also be referred to a plant obtained though mutagenesis or through the use of some new breeding techniques, whereas the single gene converted plant has essentially all of the desired morphological and physiological characteristics of the original variety in addition to the single gene or nucleotide sequence muted or engineered through the new breeding techniques.

Subject As used herein, terms such as "subject," "patient," and "mammal" are used interchangeably, and are exemplified by a human.

Susceptible to disease(s) and or insect(s). A *Justicia* plant that is susceptible to disease(s) and or insect(s) is defined as a *Justicia* plant that has the inability to restrict the growth and development of specific disease(s) and or insect(s). Plants that are susceptible will show damage when infected and are more likely to have heavy damage under moderate levels of specific disease(s) and or insect(s).

Tolerance to abiotic stresses. A *Justicia* plant that is tolerant to abiotic stresses has the ability to endure abiotic stress without serious consequences for growth, appearance and yield.

Uniformity. Uniformity, as used herein, describes the similarity between plants or plant characteristics which can be a described by qualitative or quantitative measurements.

Variety. A plant variety as used by one skilled in the art of plant breeding means a plant grouping within a single botanical taxon of the lowest known rank which can be defined by the expression of the characteristics resulting from a given genotype or combination of phenotypes, distinguished from any other plant grouping by the expression of at least one of the said characteristics and considered as a unit with regard to its suitability for being propagated unchanged (International convention for the protection of new varieties of plants). The term "cultivar" is used interchangeably with "variety" in this patent application.

Key Components of Blood. In some embodiments, the present disclosure teaches methods of extracting 'Befu' plant tissue so as to preserve the key components of blood. The term "key components of blood" as used herein refers to the following elements: Ca, Sc, Mn, Pb, Cr, Fe, V, Na, Mg, Al, Si, P, K, Ti, and Cr.

Major Components of Blood. In some embodiments, the present disclosure teaches methods of handling/processing 'Befu' plant tissue and extracts so as to preserve the major components of blood. The term "major components of blood" as used herein refers to the key components of blood as defined above together with hemoglobin contents of the 'Befu' plant.

INTRODUCTION

People are affected by many different types of blood cancers and blood conditions. Common blood disorders include anemia, bleeding disorders such as hemophilia, blood clots, and blood cancers such as leukemia, lymphoma, and myeloma. A blood substitute (also called artificial blood or blood surrogate) is a substance used to mimic and fulfill some functions of biological blood. The blood substitute provides an alternative to blood transfusion, which is transferring blood or blood-based products from one person into another. By far, there are no well-accepted oxygen-carrying blood substitutes, which is the typical objective of a red blood cell transfusion.

However, there are widely available non-blood volume expanders for cases where only volume restoration is required. These are helping doctors and surgeons avoid the risks of disease transmission and immune suppression, address the chronic blood donor shortage, and address the concerns of Jehovah's Witnesses and others who have religious objections to receiving transfused blood. The main categories of 'oxygen-carrying' blood substitutes being pursued are hemoglobin-based oxygen carriers (HBOC) and perfluorocarbon-based oxygen carriers (PFBOC). Along with continuous effort to develop oxygen therapeutics, some potential therapeutics are in clinical trials in the U.S. and Europe, and Hemopure is available in South Africa.

In one aspect, the present disclosure provides a safe alternative blood substitute candidate that can be used to treat blood disorders. This discovery resulted from identification of the unique 'Befu' plants growing in Florida and isolation of the 'Befu' extracts. When conducting inductively coupled plasma mass spectrometry (ICP-MS) analysis on the 'Befu' extracts along with a hemoglobin kit and further experiments, the plant-based potential blood substitute is disclosed herewith. Accordingly, the present disclosure provides an extract composition effective as a blood substitute and for treating known blood disorders, as health/wellness drink or food coloring amongst other potential applications.

In another aspect, the present disclose provides methods for preparing the extract composition that can be preserved under different environmental/ambient conditions and rapidly employed with key active ingredients of blood. In some embodiments, this extract is isolated and/or extracted from the 'Befu' plant tissue taught in this disclosure, further purified and enriched, as well as modified by adding other substances such as human cytochrome $b_5$ and/or analytes including but limited to Zn, Sn, O, Ni, Hg, Cd, Cu, Ti, V, and Sc.

Identification of *Justicia* Plants Designated 'Befu'

More commonly known plant species belonging to the *Justicia* genus include *Justicia Americana, Justicia brandegeeana, Justicia carnea, Justicia ovata, Justicia procumbens, Justicia pectoralis Jacq., Justicia gendarussa Buim. f., Justicia anselliana*, and *Justicia adhatoda*.

*Justicia americana* (American water-willow) is an herbaceous, aquatic flowering plant in the Acanthus family native to eastern North America north to southern Ontario, and is known as the hardiest species in the genus. It is able to survive as far north as USDA Plant Zone 4, while other members of *Justicia* genes are largely tropical and subtropical. *Justicia americana* grows up to 40 cm in height from a creeping rhizome with opposite, sessile, linear or lanceolate, and slightly crenulated leaves and bicolored flowers born in opposite arrangement on spikes 3 cm in length coming off a peduncle 10 cm in length. The flowers are colored from white to pale lavender with the upper corolla lip pale violet or white, arching over the lower lip mottled in dark purple. The lateral lobes are unadorned or slightly blushed. The anthers are purplish-red rather than the usual yellow. The fruit of this plant is a small brown capsule. The flower blooms from May to October.

*Justicia brandegeeana* (formerly *Beloperone guttata*, commonly called shrimp plant or Mexican shrimp plant) is native to Mexico and also naturalized in Florida. *Justicia brandegeeana* grows to 1 m in height and 60-90 cm in width with oval green leaves 3-7.5 cm in length. The flowers are white, extending from red bracts like a shrimp. It is hardy to −4° C. but will often recover in the spring after freezing back in USDA Plant Zone 8a. *Justicia carnea* (formerly *Jacobinia carnea*, common names including Brazilian plume flower, flamingo flower, and *jacobinia*) is native to the Atlantic Forest ecoregions of eastern Brazil and South America in southern Brazil, Paraguay and northern Argentina. *Justicia carnea* is cultivated and sold as a decorative potted plant. It is hardy to −2° C. but will often recover in the spring after freezing back in USDA Plant Zone 8a.

*Justicia procumbens* (commonly known as Water Willow) is procumbent herb with angular stems, swollen at nodes, small ovate leaves, small purple flowers in terminal spikes, inserted didynamous stamens, and shortly bilobed stigmas. Further, *Justicia procumbens* belonging to the *Justicia* genus of the Acanthaceae is an annual plant and is distributed in Korea, Japan, China, India, etc. *Justicia procumbens* has a height of about 30 cm, and its leaves are opposite and long oval in shape, 2-4 cm in length, and 1-2 cm in width. In addition, both ends of the leaf are pointed, and the edges of the leaf are elliptical or have a wave shape. The flower of the plant is light magenta in color, blooms in July to September, and bear fruit in September to October.

Varieties of some *Justicia* species are used as ornamental plants, including, e.g., *J. pictifolia* (e.g., cultivar 'Zebra;' U.S. Plant Patent No. 19,775); *J. carnea, J. jacobina* and *J. aurea* (collectively known as Brazilian plume flowers); and *J. brandegeeana* and *J. whitefielda* (collectively known as shrimp plants);

Botanical extracts of *Justicia* plants are used in methods and compositions for preventing, ameliorating or reducing a variety of human conditions and diseases, including (1) dermatological signs of aging (see, e.g., U.S. Patent Application Publication No. 2013/00552288 and WIPO Publication No. WO/2013/028266 (*J. ventricosa*)); (2) allergies (see, e.g., WIPO Publication No. WO/2016/060525); (3) HIV (see, e.g., U.S. Patent Application Publication No. 2014/0357584 and WIPO Publication No. WO/2013/019662 (*J. gendarussa*)); (4) skin lightening (see, e.g., WIPO Publication No. WO/2013/031403 (*J. procumbens*)); (5) bronchial asthma (see, e.g., WIPO Publication No. WO/2003/055558 (*J. adhatoda*)); (6) migraines (see, e.g., WIPO Publication No. WO/2007/048356 (*J. pectoralis*)); (7) for lowering cellular cholesterol and cholesteryl ester concentration (see, e.g., U.S. Pat. No. 6,365,411 (*J. wynaadensis*)); (8) cancer (see, e.g., U.S. Patent Application Publication No. 2004/0219226 and U.S. Pat. No. 7,005,146); and, (9) as a transglutaminase activator (see, e.g., U.S. Patent Application Publication No. 2015/0238404 and WIPO Publication No. WO/2014/034802 (*J. procumbens*).

The present disclosure relates to a new and distinct species of *Justicia* plants that botanically have not yet been given a scientific name, but is currently proposed by the inventor as *Justicia sanguinis*.

One new and distinct cultivar of *Justicia sanguinis* is the strain 'Befu'. 'Befu' was initially discovered in a cultivated area on private land.

Asexual reproduction via stem cuttings was performed for the new cultivar 'Befu' in a cultivated area on private land in Orlando, Fla., U.S.A. Since that time, under careful observation, the unique characteristics of the new cultivar have been uniform, stable and reproduced true to type in successive generations of asexual reproduction.

*Justicia sanguinis* has important characteristics and traits, which distinguish the new and distinct cultivars of *Justicia sanguinis* from other existing known varieties of *Justicia*.

In some embodiments, biotic and/or abiotic factors can influence hemoglobin gene expression levels in the *Justicia* plants designated 'Befu'. Also, the biotic and abiotic factors can impact the adaptation of the 'Befu' plants to harbor 'blood' in its parts including leaves, stems, and/or roots.

In some embodiments, a new extract composition from the tissue of the 'Befu' plants can be served as a blood substitute and treating blood disorders. In other embodiments, the composition contains key components of blood and which is safe. In further embodiments, the composition can be preserved for relatively long time including in ambient conditions.

Isolation of Blood Constituents from Plant Leaves

Complex multicellular organisms are equipped with specialized tissues which are concerned with the processes of nutrition and excretion. It is the primary function of blood to provide a link between various organs and cells of the body. Blood, red cells, plasma and other components maintain a constant cellular environment by circulating through every tissue and continuously delivering nutrients to the tissues and removing waste products and various tissues which are concerned with the tissue secretions from them (PHYSIOL-OGY, Third Edition, Edited by Edward E. Selkurt, Page 223, 1971). Blood is a viscous fluid composed of cells and plasma. More than 99% of the cells are red blood cells. The major function of red blood cells is to transport hemoglobin, which in turn carries oxygen from the lungs to the tissues and $CO_2$ from the tissues to the lungs. The need for a blood substitute exists for replacing blood lost by acute hemorrhage, blood losses occurring during surgical operations, resuscitation procedures after accidental blood loss, and the like. Further, as a plasma expander, a blood substitute serves as a therapeutic to treat volume deficiency shock, as an alleviant in anaphylactic and allergic shock, and for replacing plasma lost after burns and as a result of severe diarrhea.

Hemoglobin in solution has the capability to transport oxygen and, theoretically, could be used as a substitute for red blood cells. Because hemoglobin solutions are oncotically active, these solutions also expand plasma volume, thereby providing a function as a plasma expander as well. Thus the ability to be oncotically active and transport oxygen suggests that hemoglobin solutions would be desirable for a resuscitation fluid where rapid initial treatment of hypovolemia and tissue hypoxia is required. However, in order to function as an adequate resuscitation fluid, hemoglobin solutions must be capable of maintaining tissue oxygenation for specified periods of time.

Despite the importance of a proper blood substitute, blood substitutes available in the market has disadvantages over potential immune response, preservation and storage, and portability.

However, the Acanthaceae plant family is an important source of therapeutic drugs widely used in folk medicine. The present disclosure teaches that a new and distinct species of this family harbors unusually high amounts of hemoglobin and other blood components in its parts including leaves, stems and/or roots. For a long time it has been believed that plants have genes to develop hemoglobins, but mainly from the roots. This present disclosure teaches high hemoglobin concentrations from plant leaves.

The present disclosure provides a new approach for producing water-soluble blood substitute or composition from the 'Befu' plant tissue that is safe and performs vital functions of natural blood. This blood composition contains high level of hemoglobin and over 14 key analytes of blood, with customizable concentrations during the extraction process. Also, the present disclosure provides that the approach for producing the 'Befu' extracts that yield products with natural instead of artificial components as is the case with current perfluorocarbon based blood substitutes.

The present disclosure also teaches methods of isolating and/or extracting a composition comprising extracts from 'Befu' plants. In some embodiments, methods of isolation and/or extraction and approaches thereof yields a composition as a safe, blood substitute. In other embodiments, extraction and/or isolation process allows for different concentrations of blood hemoglobin and key components of blood. In further embodiments, methods of isolating and/or extracting a composition comprising extracts from 'Befu' plants provides different concentrations of blood constituents including hemoglobins and key components of blood.

In some embodiments, the method of isolating and/or extracting a composition comprising extracts from 'Befu' plants comprises (a) preparing an extract composition for treating blood disorders and other applications as described above, comprising the steps of: contacting tissue of 'Befu' plant with a water solution between about 80° F. and about 160° F., or alternatively between about 60° F. and about 180° F., which preserves the blood components and does not denature the proteins like hemoglobin. In some embodiments, the solvent water can comprise further components, such as salts, bases, acids, buffers, preservatives, or others.

In some embodiments, the solvent used to extract the 'Befu' plant is kept around 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C. In some embodiments, the solvent is kept between 1° C. and 8° C.

In some embodiments, the 'Befu' plant extraction is carried out at about 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C., including any ranges or subranges therebetween. In some embodiments, the solvent is kept between 1° C. and 8° C.

In some embodiments, the water used to extract the 'Befu' plant is at a pH suitable for preventing the denaturation of the hemoglobin protein. In some embodiments, the water used to extract the 'Befu' plant is between pH 5 and 8. In other embodiments, the pH of the water is between 6 and 7. In yet other embodiments, the water is between pH 7 and 8. In other embodiments, the pH of the water is between 7 and 11.

In some embodiments, the method of isolating and/or extracting a composition comprising extracts from 'Befu' plants comprises the step of (a) contacting tissue of the 'Befu' plant with any solvent capable of solubilizing the 'Befu' hemoglobin. In other embodiment, said composition obtained from step (a) contains all the major components of blood including hemoglobin and key components of blood. Persons having skill in the art will be familiar with standard protein extraction techniques, and will thus recognize the various solvents that could be used in the methods of the present disclosure.

In some embodiments, the method of isolating and/or extracting a composition comprising extracts from 'Befu' plants comprises (b) centrifuging the extract composition in solution obtained from step (a) at about 4,000 rpm up to about 16,000 rpm. In other embodiments, the centrifugation of the extract solution run at about 4000 rpm, about 5000 rpm, about 6000 rpm, about 7000 rpm, about 8000 rpm, about 9000 rpm, about 10000 rpm, about 11000 rpm, about 12000 rpm, about 13000 rpm, about 14000 rpm, about 15000 rpm, or about 16000 rpm. In further embodiments, the centrifugation of the extract solution run at about 12000 rpm to get optimal concentration of hemoglobin in pellet. In some embodiments, the resulting pellet is separated from the liquid phase, and either stored, or reconstituted in a smaller volume of liquid.

In some embodiments, the method of isolating and/or extracting a composition comprising extracts from 'Befu' plants comprises (c) modifying the extract i) by adding cytochrome $b_5$ human (e.g., CYB5A) to convert any methemoglobin in extract to oxy-hemoglobin and/or ii) by adding other substances and/or analytes including, but not limited to Zn, Sn, O, Ni, Hg, Cd, Cu, Ti, V, and Sc, that would enhance the extract for treating specific blood disorders. In some embodiments, the present disclosure teaches adding one or more preservatives to extracts of the 'Befu' plants. Thus in some embodiments, the present disclosure teaches the addition of citrate-phsphate-dextrose-adenine. In other embodiments, the present disclosure teaches the addition of adenine-saline.

In some embodiments the present disclosure teaches use of one or more preservatives in the 'Befu' extracts. Thus in some embodiments, the 'Befu' extracts comprise Ascorbic Acid, Ascorbyl palmitate, Benzoic Acid, Butylated hydroxyanisole (BHA), Butylated hydroxytoluene (BHT), Calcium ascorbate, Calcium propionate, Calcium sorbate, Capryllic Acid, Dilauryl thiodipropionate, Erythorbic acid, Gum guaiac, Methylparaben, Potassium bisulfite, Potassium metabisulfite, Potassium sorbate, Propionic acid, Propyl gallatepy, Propylparaben, Sodium ascorbate, Sodium benzoate, Sodium bisulfite, Sodium metabisulfite, Sodium propionate, Sodium sorbate, Sodium sulfite, Sorbic Acid, Stannous Chloride, Sulfur dioxide, Thiodipropionic acid, or Tochopherols.

In some embodiments, the method of isolating and/or extracting a composition comprising extracts from 'Befu' plants comprises (d) varying the temperature of water and other solvents, as well as the weight of tissues of 'Befu' plants such as leaves and/or stems.

In some embodiments, the method of isolating and/or extracting a composition comprising extracts from 'Befu' plants comprises (e) repeating steps (a)-(d) for highly concentrated components of blood up to whole blood levels.

In some embodiments, the method of isolating and/or extracting a composition comprising extracts from 'Befu' plants comprises (a) preparing an extract composition for treating blood disorders and other applications as described above, comprising the steps of: preparing an extract from tissues of 'Befu' plant by using water solution between about 80° F. and about 160° F., or alternatively between about 80° F. and about 160° F., or alternatively between about 60° F. and about 180° F., which preserves the blood components and does not denature the proteins like hemoglobin; (b) extracting the extract composition using any other solvents, wherein said composition obtained from step (a) contains all the major components of blood including hemoglobin and key components of blood; (c) centrifuging the extract composition in solution obtained from step (b) at about 4,000 rpm up to about 16,000 rpm; (d) modifying the extract i) by adding cytochrome $b_5$ human to convert any methemoglobin in extract to oxy-hemoglobin and/or ii) by adding other substances and/or analytes, including but not limited to Zn, Sn, O, Ni, Hg, Cd, Cu, Ti, V, and Sc, that would enhance the extract for treating specific blood disorders; (e) varying the temperature of water and other solvents, as well as the weight of tissues of 'Befu' plants such as leaves and/or stems; and (f) repeating steps (a)-(e) for highly concentrated components of blood up to whole blood levels. In other embodiments, the temperature of water solution is between about 80° F. and about 160° F., or alternatively between about 60° F. and about 180° F. In further embodiments, the centrifugation takes place higher than 10000 rpm to get optimal concentration of hemoglobin in pellet.

In further embodiments, the method of isolating and/or extracting a composition comprising extracts from 'Befu' plants further comprises lyophilizing to concentrate the extract and then reconstituting by dissolving in water to get different blood or hemoglobin concentrations up to whole blood levels. In some embodiments, the lyophilization increases concentration of hemoglobin. In some embodiments, the present disclosure teaches lyophilizing the 'Befu' extract obtained after the water or other solvent based extraction. In other embodiments, the lyophilization occurs after the centrifugation step. Persons having skill in the art will be capable of optimizing the parameters of their lyophilization protocol/machinery. In some embodiments, the present disclosure teaches lyophilization at −50° C. for 3 h with a cooling rate of 1° C./min; with primary drying, −50° C. for 60 h at 3 Pa; and secondary drying, 0° C. for 4 h and 20° C. for 8 h at 3 Pa.

In some embodiments, the method of isolating and/or extracting a composition comprising extracts from 'Befu' plants can be applied to the whole 'Befu' plant and/or plant parts such as leaves, stems, roots, buds, blossoms, flowers, seeds, and the like.

In other embodiments, the extract fractions can be mixed and/or blended with each other and the mixture can be highly concentrated before use.

In other embodiments, rapid extraction and/or isolation process can be pursued and done in less than 5 minutes, ready for use in emergency situations or settings such as emergency room in hospital where there is an urgent need of blood or blood substitute.

In further embodiments, the extracts disclosed herein, may additionally comprise other complementary plant tissue extracts and composition as well as modifiers to enhance their utility.

In some embodiments, the extract can also be obtained by i) washing tissue from the 'Befu' plant, such as leaves, stems, or roots, ii) drying the washed tissue at low heat setting to maintain blood composition, iii) physically crushing dried or fresh tissue from the 'Befu' plants and iv) extracting the crushed material with an extraction solvent including water and/or similar solvents such as PBS. In other embodiments, the washed tissue can be completely dried. In further embodiments, As the extraction solvent, any conventional extraction solvent can be used. In further embodiments, the extract can be obtained by performing extraction at any temperature.

In some embodiments, the extract composition from tissue of the 'Befu' plants allow modification with general food additives, including a softener, a fragrance, a preservative and an antioxidant if needed. In other embodiments, the extract composition from tissue of the 'Befu' plants is utilized as a color additive for changing food coloring and alternatively can be combined with other general food additives, such as, for example, a softener, a fragrance, a preservative and/or an antioxidant for its own purpose.

Preservation of 'Befu' Extracts

A major issue faced in blood transfusion is the preservation of blood. This present disclosure provides an approach and solution for preserving the product outside of the refrigerator, ready for applications. For instance, there is a need of supplying blood and/or blood substitute abruptly in battlefield which may be far away from needed storage areas. It is critical to keep and store blood substrate in room temperature and/or above refrigeration temperature to provide hemoglobin and other blood constituents to the needy patients in a short amount of time.

The present disclosure teaches that the hemoglobin concentration of 'Befu' extract is adequately preserved by methods taught herein. The hemoglobin concentration of the 'Befu' extract reduces over time if not adequately preserved. The present disclosure provides two approaches to preserve high concentrations over time to allow rapid reconstitution: 1) gradual drying of 'Befu' plant tissues including leaves, stems, and/or roots at low temperature that is less than 40° C. or alternatively less than 45; and 2) lyophilization of 'Befu' plant extract.

In some embodiments, 'Befu' plant leaves are gradually dried at low temperature up to 40° C. or alternatively 45° C.

In some embodiments, specific gentle heating temperatures are chosen to prevent the plant tissue from rotting but yet enough to preserve all key components of the blood. This method of preservation will allow for rapid extraction when needed. In some embodiments, methods for gradual drying of 'Befu' tissue to preserve all key components of the blood, including lyophilization, use solar and other gradual heat sources over many days to ensure preservation of key components.

In some embodiments, 'Befu' plant extract by methods described above is lyophilized for preservation. In some embodiments, the product can be readily transported and reconstituted for use such as in emergency rooms, battle filed, or high trauma zones. The present disclosure teaches that preservation approach yields 'Befu' plant extract as blood substitute that can be easily portable and remain viable to be employed in different situations such as room/ambient conditions or other extreme conditions. Dried and/or lyophilized preservation sample allows rapid conversion to blood substitute with modifiers for different applications.

In some embodiments, the 'Befu' extract can be stored and/or preserved under various conditions for significantly much longer time than other transfusable blood substitute, and can be kept at room temperature. In further embodiments, the 'Befu' extract as the blood substitute disclosed herein does not need a refrigerator or other special conditions to preserve it. In some embodiments, the 'Befu' extract can be preserved in any conditions, temperature cold or warm or hot, which makes it very portable.

APPLICATIONS AND USES

The potential toxicity of unstablized hemoglobin towards human kidneys, when used directly, has severely limited its application as a red blood cell substitute and in cancer treatments. However, the 'Befu' plant extract is already stabilized and non-toxic and does not need to be conjugated with other polymers to minimize toxicity as currently being attempted by competing blood substitute development efforts.

The benefits of the plant-based blood substitute and its composition is that blood donation from humans or animals is not required and that the plant-based blood substitute and its composition are expected to be universal, thus being compatible with all blood-type groups.

Furthermore, high levels of hemoglobin and other blood analytes are obtained from a plant tissue extract as disclosed herein.

The present disclosure teaches that a safe blood substitute produced from a new plant species 'Befu' by methods taught in this disclosure can be used for: high-risk patients; high stress environments; immunocompromised or chemotherapy patients; and patients where standard donor blood carries a risk including patients who have had previous transfusion related adverse events. There are major safety concerns with currently available blood substitutes due to the methods and approaches of production thereof. The approach for producing the 'Befu' results in a blood composition that could be used by any patient. Other applications of 'Befu' are expected for treating various blood disorders including: anemia, bleeding disorders such as hemophilia, blood clots, and blood cancers such as leukemia, lymphoma, and myeloma. A major advantage is that the extraction or preservation results in a safe blood substitute.

In some embodiments, methods of extraction and preservation yields superior safe blood substitute and composition potential use: a) cancer treatment, b) treatment of trauma or other health conditions related to blood loss, c) application in blood transfusion with major impact in the blood transfusion market, d) blood disorders treatment with minimal toxicity or side effects, e) a health drink/remedy for treating blood disorders, and f) a food color additive.

The extract disclosed herein can be used for blood substitutes or alternatives to transfused blood for the treatment of acute blood loss (such as in trauma or surgery).

Great benefit could be derived from the rapid treatment of patients in trauma situations. Because these blood substitutes do not contain any of the antigens that determine blood type, 'Befu' (U— for universal) can be used 'universally' across all types without immunologic reaction.

Befu extracts are relatively non-toxic compared to other blood substitutes under development. In some embodiments, blood disorders include: anemia, bleeding disorders such as hemophilia, blood clots, and blood cancers such as leukemia, lymphoma, and myeloma. In some embodiments, the 'Befu' extract can be used as a blood substitute to avoid the risks of disease transmission and immune suppression, address the chronic blood donor shortage, and address the concerns of Jehovah's Witnesses and others who have religious objections to receiving transfused blood.

In some embodiments, the apparent non-toxic effect of 'Befu' extract, containing high levels of hemoglobin and other blood constituents, is useful for developing biomedical and food industry applications. Potential applications include: treatment of blood disorders, use in food coloring or nutraceuticals, and for developing blood substitutes from plants, which can mimic or fulfill some functions of human blood in trauma medicine.

Blood Cancer

Blood cancer refers to a class of cancers that attack the blood, bone marrow, and/or lymphatic system. This class of cancers includes leukemia and multiple myeloma, all of which can be life-threatening diseases for which new and more efficacious treatments are needed.

The relation between cancer cells and the tumor microenvironment affects the growth and survival of cancer cells (see Hiruma et al., *Blood*. 2009; 113(20): 4894-4902, and Podar et al., *Leukemia*. 2009; 23(1): 10-24, each of which is incorporated herein by reference). Hypoxia, or low oxygen level, is a characteristic of the microenvironment of many solid tumors and results from the poor vascularization that characterizes many solid tumors. High metastatic potential and poor prognosis correlate highly with hypoxia in solid tumors.

As used herein, "blood cancer" refers to a hematological malignancy involving abnormal hyperproliferation or malignant growth and/or metastasis of a blood cell. Blood cancers include, without limitation, acute leukemias (AML and ALL), chronic leukemias (CML and CLL), idiopathic myelofibrosis (MF, also known as agnogenic myeloid metaplasia or AMM), lymphoma, myelodysplastic syndrome (MDS), and multiple myeloma (MM). Acute Lymphoblastic Leukemia (ALL)" refers to a blood cancer, particularly a cancer affecting the white blood cells, and is characterized by hyperproliferation of lymphoblasts. In ALL, malignant, immature white blood cells continuously multiply and are overproduced in the bone marrow. ALL cells crowd out normal cells in the bone marrow and may metastasize to other organs. ALL is also known as acute lymphocytic leukemia and acute childhood leukemia.

"Acute Myeloid (Myelogenous) Leukemia (AML)" refers to a blood cancer in which white blood cells known as "myeloid cells" become cancerous. In AML, the bone marrow produces abnormal blood cells called "myeloblasts," leading to the replacement of normal blood cells with abnormal cells and disrupting the normal function of the bone marrow. With the abnormal production of "blast" cells, the production of normal blood marrow cells is inhibited, causing a deficiency of red blood cells, normal white blood cells, and platelets, leading to deleterious effects such as anemia, vulnerability to bruising and bleeding, and increased risk of infection.

"Chronic lymphocytic (or lymphoid) leukemia (CLL)" refers to a blood cancer affecting B cell lymphocytes. B cells originate in the bone marrow and develop in the lymph nodes. In CLL, the B cells grow in an uncontrolled manner and accumulate in the bone marrow and blood, wherein they crowd out healthy blood cells. As the disease advances, CLL results in swollen lymph nodes, spleen, and liver.

"Chronic myelogenous leukemia (CML)" refers to a blood cancer in which the bone marrow produces granulocytes, some of which never mature into white blood cells. The "immature" white blood cells are called "blasts." Over time, the granulocytes and blasts grow out of control and result in a platelet and red blood cell deficiency in the bone marrow. CML patients may have a gene mutation called the "Philadelphia chromosome." This chromosome causes the bone marrow to make certain tyrosine kinases that result in the development of granulocytes or blasts. Some CML patients have a form of the disease resistant to treatment with tyrosine kinase inhibitors. CML includes, without limitation, chronic myelogenous leukemia, chronic myeloid leukemia, chronic myelocytic leukemia, and chronic granulocytic leukemia (CGL).

"Multiple myeloma (MM)" refers to a blood cancer having clonal B cell malignancy characterized by the accumulation of neoplastic plasma cells in the bone marrow. There are several types of multiple myeloma, including smoldering multiple myeloma (SMM), plasma cell leukemia, nonsecretory myeloma, osteosclerotic myeloma (POEMS syndrome), solitary plasmacytoma (also called solitary myeloma of the bone), and extramedullary plasmacytoma.

"Myelodysplastic syndrome (MDS)" refers to a blood cancer that occurs when the bone marrow stops producing healthy blood cells and instead produces immature blood cells that function poorly. This results in the production of too many defective blood cells and not enough healthy blood cells. In people with MDS, the disorder begins when a defect occurs in a stem cell in the bone marrow. That stem cell, in turn, produces blood cells that carry the same defect. These defective cells grow to outnumber healthy blood cells and live longer. These defective cells may also kill other stem cells too early, resulting in low blood counts. The abnormal cells also crowd out the healthy cells. MDS can progress over time into acute myelogenous leukemia.

"Myelofibrosis" refers to a type of chronic leukemia that disrupts the body's normal production of blood cells. Myelofibrosis can occur on its own (primary myelofibrosis) or it can occur as a result of another bone marrow disorder (secondary myelofibrosis). Advanced myelofibrosis gets progressively worse and can eventually develop into a more serious form of leukemia.

In some embodiments, the 'Befu' extract as the blood substitute is capable of treating blood cancer including but not limited to acute leukemias (AML and ALL), chronic leukemias (CML and CLL), idiopathic myelofibrosis (MF, also known as agnogenic myeloid metaplasia or AMM), lymphoma, myelodysplastic syndrome (MDS), and multiple myeloma (MM). In other embodiments, the blood substitutes, the 'Befu' extract as the blood substitute can treat acute leukemias (AML and ALL), chronic leukemias (CML and CLL), idiopathic myelofibrosis (MF, also known as agnogenic myeloid metaplasia or AMM), lymphoma, myelodysplastic syndrome (MDS), and multiple myeloma (MM).

Blood Disorder

As used herein "blood disorder" includes disorders any disorder of the blood and blood-forming organs. The term blood disorder includes nutritional anemias (e.g., iron deficiency anemia, sideropenic dysphasia, Plummer-Vinson syndrome, vitamin $B_{12}$ deficiency anemia, vitamin $B_{12}$ deficiency anemia due to intrinsic factor, pernicious anemia, folate deficiency anemia, and other nutritional anemias), myelodysplastic syndrome, bone marrow failure or anemia resulting from chemotherapy, radiation or other agents or therapies, hemolytic anemias (e.g., anemia due to enzyme disorders, anemia due to phosphate dehydrogenase (G6PD) deficiency, favism, anemia due to disorders of glutathione metabolism, anemia due to disorders of glycolytic enzymes, anemias due to disorders of nucleotide metabolism and anemias due to unspecified enzyme disorder), thalassemia (α-thalassemia, β-thalassemia, δβ-thalassemia, thalassemia trait, hereditary persistence of fetal hemoglobin (HPFP), and unspecified thalassemias), sickle cell disorders (sickle cell anemia with crisis, sickle cell anemia without crisis, double heterozygous sickling disorders, sickle cell trait and other sickle cell disorders), hereditary hemolytic anemias (hereditary spherocytosis, hereditary elliptocytosis, other hemaglobinopathies and other specified hereditary hemolytic anemias, such as stomatocyctosis), acquired hemolytic anemia (e.g., drug-induced autoimmune hemolytic anemia, other autoimmune hemolytic anemias, such as warm autoimmune hemolytic anemia, drug-induced non-autoimmune hemolytic anemia, hemolytic-uremic syndrome, and other non-autoimmune hemolytic anemias, such as microangiopathic hemolytic anemia); aplastic anemias (e.g., acquired pure red cell aplasia (erythroblastopenia), other aplastic anemias, such as constitutional aplastic anemia and fanconi anemia, acute posthemorrhagic anemic, and anemias in chronic diseases), coagulation defects (e.g., disseminated intravascular coagulation (difibrination syndrome)), hereditary factor VIII deficiency (hemophilia A), hereditary factor IX deficiency (Christmas disease), and other coagulation defects such as Von Willebrand's disease, hereditary factor XI deficiency (hemophilia C), purpura (e.g., qualitative platelet defects and Glanzmann's disease), neutropenia, agranulocytosis, functional disorders of polymorphonuclear neutrophils, other disorders of white blood cells (e.g., eosinophilia, leukocytosis, lymophocytosis, lymphopenia, monocytosis, and plasmacyctosis), diseases of the spleen, methemoglobinemia, other diseases of blood and blood forming organs (e.g., familial erythrocytosis, secondary polycythemia, essential thrombocytosis and basophilia), thrombocytopenia, infectious anemia, hypoproliferative or hypoplastic anemias, hemoglobin C, D and E disease, hemoglobin lepore disease, and HbH and HbS diseases, anemias due to blood loss, radiation therapy or chemotherapy, or thrombocytopenias and neutropenias due to radiation therapy or chemotherapy, sideroblastic anemias, myelophthisic anemias, antibody-mediated anemias, and certain diseases involving lymphoreticular tissue and reticulohistiocytic system (e.g., Langerhans' cell hysticiocytosis, eosinophilic granuloma, Hand-Schuiller-Christian disease, hemophagocytic lymphohistiocytosis, and infection-associated hemophagocytic syndrome).

In some embodiments, the 'Befu' extract described herein can treat, prevent, or otherwise ameliorate blood disorders described above.

In other embodiments, the 'Befu' extract of the disclosure is useful in the treatment of anemias including, without limitation: blood loss anemias such as post-hemorrhagic anemia; 1) anemias caused by faulty RBC production, such as achrestic anemia, anemia due to renal disease, aplastic anemia, congenital dyserythropoietic anemia, congenital spherocytic anemia, Diamond-Blackfan anemia, Fanconi anemia, Glucose-6-Phosphate Dehydrogenase (G6PD) Deficiency, Hereditary xerocytosis, hexokinase deficiency, hyperchromic anemia, macrocytic anemia, megaloblastic anemia, megaloblastic hereditary anemia, microcytic anemia, Minkowski-Chauffard syndrome, myelophthisic anemia, normocytic anemia, Pearson's anemia, pernicious anemia, sickle cell disease, sideroblastic anemia, sideropenic anemia, Southeast Asian ovalocytosis, Thalassemia (alpha, beta, delta), Von Jaksh's anemia and Hemoglobin E disease; and 2) anemias caused by RBC destruction, such as acquired hemolytic anemia, autoimmune hemolytic anemia, Choreaacanthocytosis, congenital hemolytic anemia, drug-induced hemolytic anemia, hemolytic uremic syndrome, hereditary elliptocytosis, hereditary pyropoikilocytosis, hereditary spherocytosis, hereditary stomatocytosis, Lederer's anemia, microangiopathic hemolytic anemia, paroxysmal nocturnal hemoglobinuria, poikilocytic anemia, pyruvate kinase deficiency, Rh deficiency syndrome, spherocytic anemia, spur cell hemolytic anemia, spur-cell anemia, Triosephosphate isomerase (TPI) deficiency and Warm autoimmune hemolytic anemia.

Cancer

The term "Cancer" or "cancerous" is used to refer to a physiological condition that is characterized by unregulated cell growth. In some embodiments, cancer refers to a tumor. "Tumor" is used to refer to any neoplastic cell growth or proliferation or any pre-cancerous or cancerous cell or tissue. A tumor may be malignant or benign. Types of cancer include, but are not limited to, adrenal cancer, adrenocortical carcinoma, anal cancer, appendix cancer, bile duct cancer, bladder cancer, bone cancer (e.g., Ewing sarcoma tumors, osteosarcoma, malignant fibrous histiocytoma), brain cancer (e.g., astrocytomas, brain stem glioma, craniopharyngioma, ependymoma), bronchial tumors, central nervous system tumors, breast cancer, Castleman disease, cervical cancer, colon cancer, rectal cancer, colorectal cancer, endometrial cancer, esophageal cancer, eye cancer, gallbladder cancer, gastrointestinal cancer, gastrointestinal carcinoid tumors, gastrointestinal stromal tumors, gestational trophoblastic disease, heart cancer, Kaposi sarcoma, kidney cancer, largyngeal cancer, hypopharyngeal cancer, leukemia (e.g., acute lymphoblastic leukemia, acute myeloid leukemia, chronic lymphocytic leukemia, chronic myelogenous leukemia), liver cancer, lung cancer, lymphoma (e.g., AIDS-related lymphoma, Burkitt lymphoma, cutaneous T cell lymphoma, Hodgkin lymphoma, Non-Hodgkin lymphoma, primary central nervous system lymphoma), malignant mesothelioma, multiple myeloma, myelodysplastic syndrome, nasal cavity cancer, paranasal sinus cancer, nasopharyngeal cancer, neuroblastoma, oral cavity cancer, oropharyngeal cancer, osteosarcoma, ovarian cancer, pancreatic cancer, penile cancer, pituitary tumors, prostate cancer, retinoblastoma, rhabdomyosarcoma, rhabdoid tumor, salivary gland cancer, sarcoma, skin cancer (e.g., basal cell carcinoma, melanoma), small intestine cancer, stomach cancer, teratoid tumor, testicular cancer, throat cancer, thymus cancer, thyroid cancer, unusual childhood cancers, urethral cancer, uterine cancer, uterine sarcoma, vaginal cancer, vulvar cancer, Waldenstrom macrogloblulinemia, and Wilms tumor. Side effects of cancer treatment may include, but are not limited to, opportunistic autoimmune disorder(s), systemic toxicity, anemia, loss of appetite, irritation of bladder lining, bleeding and bruising (thrombocytopenia), changes in taste or smell, constipation, diarrhea, dry mouth, dysphagia, edema, fatigue, hair loss (alopecia), infection, infertility, lymphedema, mouth sores, nausea, pain, peripheral neuropathy, tooth decay, urinary tract infections, and/or problems with memory and concentration (National Cancer Institute).

In some embodiments, the 'Befu' extract described herein may treat cancer described herein.

Tea and Tea-Like Beverages

As used herein, a "tea" or "tea-type beverage" refer generally to any drink made by infusing plant parts in water. Typically, the infusion takes place in hot, very hot or boiling water, which may be consumed hot, warm, at room temperature, chilled or cold. Generally, a tea is made by infusing the dried, crushed leaves of the plant in boiling water. A tea or tea-type beverage, also known as "infusions" or "tisanes," can easily be made from herbs, medicinal plants or tea plants (*Camellia sinensis*) by putting all or parts of the fruits, herbs, medicinal plants, or tea (such as, for example, in the form of leaves or powder) in a cup of hot or boiling water. For some teas, such as fruit teas or teas made from herbs or medicinal plants, the steep time is rather long, whereas for various kinds of tea plants, maintaining a certain steep time is required for producing the best flavor. The flavor and taste can depend greatly depends on water quality and temperature.

Tea is generally prepared as green leaf tea or black leaf tea. The method of preparing such teas is well known to those skilled in the art. Generally, to prepare black leaf tea, fresh green leaves of a plant are subjected to mild drying, comminuted, fermented (in which enzymes in the leaf tea oxidize various substrates to produce brown-colored products) and then fired (to dry the tea leaves). In some embodiments, no fermentation process is used to produce the tea.

Green leaf tea is not exposed to the fermentation process. Partial fermentation may be used to produce intermediate-type teas known as "oolong" tea.

In some embodiments, tea based beverages can be prepared by methods other than infusing leaves in hot water and served in ways other than poured from tea pots. For example they can be made with concentrates or powders that are mixed with hot water in vending machines or used to prepare ready to drink teas in cans and bottles. Some tea products involve accelerated infusion, enhanced colors, and added aromas.

For examples and descriptions of teas and the processes to make teas, see, e.g., U.S. Published Patent Application Nos. 2014/0295049, 2008/0095913 and 2008/0107774; and, Keating and Long. How to Make Tea: The Science Behind the Leaf (How to Make Series), 2015, Ivy Press.

In some embodiments, health drinks such as teas and tea-like beverages can be a remedy for treating various blood disorders, including but not limited to anemia, bleeding disorders such as hemophilia, blood clots, and blood cancers such as leukemia, lymphoma, and myeloma.

In some embodiments, the 'Befu' extract described herein may be used in tea and tea-like beverages as described herein.

Food and Health Supplements

In addition to health drinks, the 'Befu' extracts of the present disclosure may be used in foodstuffs. Such 'Befu' extracts may be combined with any other foodstuff, for example, dairy products such as butter, cheese, yogurt, milk, and plant-based milk; any oil-based food such as margarine, mayonnaise or peanut butter; baked goods, cereals, pastas; a variety of water-based foodstuffs, such as drinks, including health drink mixes, tea-like beverage as discussed above.

Also, the 'Befu' extracts may be used in health supplements including but are not limited to the vitamins such as vitamin A, vitamin C, vitamin E, riboflavin, niacin, niacinamide, pantothenic acid, pyridoxine, cobalamin, biotin, inositol, choline bitartrate, betaine, and vitamin K and minerals such as molybdenum, chromium and potassium.

This present disclosure is broadly directed to the addition of the 'Befu' extracts as additional supplement to other health supplements containing assimilable iron compounds, vitamins, minerals or mixtures thereof, and to the addition of the 'Befu' extracts to various base food products.

In some embodiments, the 'Befu' extract can be used as a food/health supplement and additive to prepare food products, health supplements or drinks effective for treating various blood disorders.

Food Colorant

The form that can be assumed by the colored foods of the present disclosure is not particularly limited as long as they are foods colored with dyes. It should, however, be noted that the utility of the present disclosure is increased in foods that are prone to fade in color if they do not contain antifading agents. Examples of the colored foods of the present disclosure include: beverages; milk beverages; alcoholic beverages; foods such as cooked rice, cereals (e.g., rice, wheat, barley, maize, foxtail millet, millet), bread, other wheat flour products, noodles, roux for curry or stew, frozen foods, chilled foods, retorted foods, dairy products (e.g. ice cream), and processed milk products; beverages such as milk, soft drinks, carbonated drinks, green tea, black tea, oolong tea, coffee, cocoa, refined sake, beer, low-malt beer, synthetic refined sake, mirin (sweet cooking rice wine), wine, shochu (Japanese distilled spirit), whiskey, and vegetable juice; seasonings such as miso (bean paste), shoyu (soy sauce), vinegar, seasonings for umami, dressings, sauce, and mayonnaise; processed marine foods such as fish paste products, fish ham, sausages, katsuobushi (dried bonito), tsukudani (food boiled in soy sauce); frozen foods such as cooked rice, noodles, croquette, hamburg steak, steamed Chinese dumplings, Japanese pan-fried dumplings, or gratin, all being in frozen state; instant foods such as instant noodles, instant soup, instant curry, instant miso soup, and instant coffee; and confections such as Japanese confectionery (including unbaked or half-baked), Western confectionery (including unbaked or half-baked), candies, chocolates, chewing gums, biscuits, rice confectionery, snack packs, oiled confectionery, and miscellaneous confectionery.

In some embodiments, the 'Befu' extract can be used as a food colorant and/or a food color additive.

Use of 'Befu' Extracts in Meat Substitute Products

In some embodiments, the present disclosure teaches the use of 'Befu' extracts for producing vegetarian meat substitutes. Thus, in some embodiments, the present disclosure teaches the use of 'Befu' hemoglobin as a food additive in meat substitutes, such as those disclosed in U.S. Pat. Nos. 10,039,306, 9,943,096, 9,938,327, 9,833,768, 9,826,772, 9,808,029, 9,737,875, 9,700,067, and 9,011,949, each of which is hereby incorporated by reference in its entirety for all purposes.

In some embodiments, the present disclosure features a method for producing a hemoglobin flavoring compound. In some embodiments, the method can include combining an iron complex (e.g., a heme moiety, such as a hemoglobin) and one or more flavor precursor molecules to form a mixture, the one or more flavor precursor molecules selected from the group consisting of glucose, fructose, arabinose, ribose glucose-6-phosphate, fructose 6-phosphate, fructose 1,6-diphosphate, inositol, maltose, sucrose, maltodextrin, glycogen, nucleotide-bound sugars, molasses, a phospholipid, a lecithin, inosine, inosine monophosphate (IMP), guanosine monophosphate (GMP), pyrazine, adenosine monophosphate (AMP), lactic acid, succinic acid, glycolic acid, thiamine, creatine, pyrophosphate, vegetable oil, algal oil, corn oil, soybean oil, palm fruit oil, palm kernel oil, safflower oil, flaxseed oil, rice bran oil, cottonseed oil, canola oil, olive oil, sunflower oil, flaxseed oil, coconut oil, mango oil, a free fatty acid, cysteine, methionine, isoleucine, leucine, lysine, phenylalanine, threonine, tryptophan, valine, arginine, histidine, alanine, asparagine, aspartate, glutamate, glutamine, glycine, proline, serine, tyrosine, glutathione, an amino acid derivative, a protein hydrolysate, a malt extract, a yeast extract, and a peptone; and heating the mixture to form one or more flavor compounds selected from the group consisting of phenylacetaldehyde, 1-octen-3-one, 2-n-heptylfuran, 2-thiophenecarboxaldehyde, 3-thiophenecarboxaldehyde, butyrolactone, 2-undecenal, pyrazine, methyl-, furfural, 2-decanone, pyrrole, 1-octen-3-ol, 2-acetylthiazole, (E)-2-octenal, decanal, benzaldehyde, (E)-2-nonenal, pyrazine, 1-hexanol, 1-heptanol, dimethyl trisulfide, 2-nonanone, 2-pentanone, 2-heptanone, 2,3-butanedione, heptanal, nonanal, 2-octanone, 1-octanol, 3-ethylcyclopentanone, 3-octen-2-one, (E,E)-2,4-heptadienal, (Z)-2-heptenal, 2-heptanone, 6-methyl-, (Z)-4-heptenal, (E,Z)-2,6-nonadienal, 3-methyl-2-butenal, 2-pentyl-furan, thiazole, (E,E)-2,4-decadienal, hexanoic acid, 1-ethyl-5-methylcyclopentene, (E,E)-2,4-nonadienal, (Z)-2-decenal, dihydro-5-pentyl-2(3H)-furanone, trans-3-nonen-2-one, (E,E)-3,5-octadien-2-one, (Z)-2-octen-1-ol, 5-ethyldihydro-2(3H)-furanone, 2-butenal, 1-penten-3-ol, (E)-2-hexenal, formic acid, heptyl ester, 2-pentyl-thiophene, (Z)-2-nonenal, 2-hexyl-thiophene, (E)-2-decenal, 2-ethyl-5-methyl-pyrazine, 3-ethyl-2,5-dimethyl-pyrazine, 2-ethyl-1-hexanol, thiophene, 2-methyl-furan, pyridine, butanal, 2-ethyl-furan, 3-methyl-butanal, trichloromethane, 2-methyl-butanal, methacrolein, 2-methyl-propanal, propanal, acetaldehyde, 2-propyl-furan, dihydro-5-propyl-2(3H)-furanone, 1,3-hexadiene, 4-decyne, pentanal, 1-propanol, heptanoic acid, trimethyl-ethanethiol, 1-butanol, 1-penten-3-one, dimethyl sulfide, 2-ethyl furan, 2-pentyl-thiophene, 2-propenal, 2-tridecen-1-ol, 4-octene, 2-methyl thiazole, methyl-pyrazine, 2-butanone, 2-pentyl-furan, 2-methyl-propanal, butyrolactone, 3-methyl-butanal, methyl-thiirane, 2-hexyl-furan, butanal, 2-methyl-butanal, 2-methyl-furan, furan, octanal, 2-heptenal, 1-octene, formic acid heptyl ester, 3-pentyl-furan, and 4-penten-2-one.

In another aspect, this document features a method for producing a flavor compound. The method includes combining an iron complex, such as a heme-containing protein (e.g., hemoglobin from the 'Befu' plant), and one or more flavor precursor molecules to form a mixture, the one or more flavor precursor molecules selected from the group consisting of glucose, fructose, ribose, arabinose, glucose-6-phosphate, fructose 6-phosphate, fructose 1,6-diphosphate, inositol, maltose, sucrose, maltodextrin, glycogen, nucleotide-bound sugars, molasses, a phospholipid, a lecithin, inosine, IMP, GMP, pyrazine, AMP, lactic acid, succinic acid, glycolic acid, thiamine, creatine, pyrophosphate, vegetable oil, algal oil, corn oil, soybean oil, palm fruit oil, palm kernel oil, safflower oil, flaxseed oil, rice bran oil, cottonseed oil, olive oil, sunflower oil, canola oil, flaxseed oil, coconut oil, mango oil, a free fatty acid, methionine, cysteine, isoleucine, leucine, lysine, phenylalanine, threonine, tryptophan, valine, arginine, histidine, alanine, asparagine, aspartate, glutamate, glutamine, glycine, proline, serine, tyrosine, glutathione, an amino acid derivative, a protein hydrolysate, a malt extract, a yeast extract, and a peptone; and heating the mixture to form one or more flavor. For example, the flavor precursors can include cysteine, a sugar, and one or more other precursors.

This document also features a method for imparting a meat like flavor (e.g., beef-like, chicken like, pork-like, lamb-like, turkey-like, duck-like, deer-like, or bison-like) to a food product. The method includes contacting a food product with a flavoring composition, the flavoring composition comprising i) an iron complex, such as a heme moiety (e.g., a heme-containing protein, such as hemoglobin from the 'Befu' plant); and ii) one or more flavor precursor molecules selected from the group consisting of glucose, fructose, ribose, arabinose, glucose-6-phosphate, fructose 6-phosphate, fructose 1,6-diphosphate, inositol, maltose, sucrose, maltodextrin, glycogen, nucleotide-bound sugars, molasses, a phospholipid, a lecithin, inosine, IMP, GMP, pyrazine, AMP, lactic acid, succinic acid, glycolic acid, thiamine, creatine, pyrophosphate, vegetable oil, algal oil, corn oil, soybean oil, palm fruit oil, palm kernel oil, safflower oil, flaxseed oil, rice bran oil, cottonseed oil, olive oil, sunflower oil, canola oil, flaxseed oil, coconut oil, mango oil, a free fatty acid, cysteine, methionine, isoleucine, leucine, lysine, phenylalanine, threonine, tryptophan, valine, arginine, histidine, alanine, asparagine, aspartate, glutamate, glutamine, glycine, proline, serine, tyrosine, glutathione, an amino acid derivative, a protein hydrolysate, a malt extract, a yeast extract, and a peptone; wherein after heating the food product and the flavoring composition together, a meat like flavor (e.g., beef-like, chicken like, pork-like, lamb-like, turkey-like, duck-like, deer-like, or bison-like) is imparted to the food product.

*Justicia* Breeding

The goal of *Justicia* breeding is to develop new, unique and superior *Justicia* strains, varieties, cultivars and hybrids. The breeder initially selects and crosses two or more parental lines, followed by repeated selfing and selection, producing many new genetic combinations. Another method used to develop new, unique and superior *Justicia* cultivar occurs when the breeder selects and crosses two or more parental lines followed by haploid induction and chromosome doubling that result in the development of dihaploid cultivars. The breeder can theoretically generate billions of different genetic combinations via crossing, selfing and mutations and the same is true for the utilization of the dihaploid breeding method.

Each year, the plant breeder selects the germplasm to advance to the next generation. This germplasm is grown under unique and different geographical, climatic and soil conditions, and further selections are then made, during and at the end of the growing season. The cultivars developed are unpredictable. This unpredictability is because the breeder's selection occurs in unique environments, with no control at the DNA level (using conventional breeding procedures or dihaploid breeding procedures), and with millions of different possible genetic combinations being generated. A breeder of ordinary skill in the art cannot predict the final resulting cultivars he develops, except possibly in a very gross and general fashion. This unpredictability results in the expenditure of large research monies to develop superior new *Justicia* cultivars.

The development of commercial *Justicia* cultivars requires the development and selection of *Justicia* plants, the crossing of these plants, and the evaluation of the crosses.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes or through the dihaploid breeding method followed by the selection of desired phenotypes. The new cultivars are evaluated to determine which have commercial potential.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection, and backcross breeding.

i Pedigree Selection

Pedigree breeding is used commonly for the improvement of self-pollinating crops or inbred lines of cross-pollinating crops. Two parents possessing favorable, complementary traits are crossed to produce an F1. An F2 population is produced by selfing one or several F1s or by intercrossing two F1s (sib mating). The dihaploid breeding method could also be used. Selection of the best individuals is usually begun in the F2 population, then, beginning in the F3, the best individuals in the best families are selected. Replicated testing of families, or hybrid combinations involving individuals of these families, often follows in the F4 generation to improve the effectiveness of selection for traits with low heritability. At an advanced stage of inbreeding (i.e., F6 and F7), the best lines or mixtures of phenotypically similar lines are tested for potential release of new cultivars. Similarly, the development of new cultivars through the dihaploid system requires the selection of the cultivars followed by two to five years of testing in replicated plots.

ii Backcross Breeding

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

When the term *Justicia* cultivar is used in the context of the present disclosure, this also includes any *Justicia* cultivar plant where one or more desired trait has been introduced through backcrossing methods, whether such trait is a naturally occurring one, a mutant or a gene or a nucleotide sequence modified by the use of New Breeding Techniques. Backcrossing methods can be used with the present disclosure to improve or introduce one or more characteristic into the *Justicia* cultivar of the present disclosure. The term "backcrossing" as used herein refers to the repeated crossing of a hybrid progeny back to the recurrent parent, i.e., backcrossing one, two, three, four, five, six, seven, eight, nine, or more times to the recurrent parent. The parental *Justicia* cultivar plant which contributes the gene or genes for the desired characteristic is termed the nonrecurrent or donor parent. This terminology refers to the fact that the nonrecurrent parent is used one time in the backcross protocol and therefore does not recur. The parental *Justicia* cultivar to which the gene or genes from the nonrecurrent parent are transferred is known as the recurrent parent as it is used for several rounds in the backcrossing protocol.

In a typical backcross protocol, the original cultivar of interest (recurrent parent) is crossed to a second cultivar (nonrecurrent parent) that carries the gene or genes of interest to be transferred. The resulting progeny from this cross are then crossed again to the recurrent parent and the process is repeated until a *Justicia* plant is obtained wherein all the desired morphological and physiological characteristics of the recurrent parent are recovered in the converted plant, generally determined at a 5% significance level when grown in the same environmental conditions, in addition to the gene or genes transferred from the nonrecurrent parent. It has to be noted that some, one, two, three or more, self-pollination and growing of population might be included between two successive backcrosses. Indeed, an appropriate selection in the population produced by the self-pollination, i.e. selection for the desired trait and physiological and morphological characteristics of the recurrent parent might be equivalent to one, two or even three additional backcrosses in a continuous series without rigorous selection, saving then time, money and effort to the breeder. A non-limiting example of such a protocol would be the following: a) the first generation F1 produced by the cross of the recurrent parent A by the donor parent B is backcrossed to parent A, b) selection is practiced for the plants having the desired trait of parent B, c) selected plant are self-pollinated to produce a population of plants where selection is practiced for the plants having the desired trait of parent B and physiological and morphological characteristics of parent A, d) the selected plants are backcrossed one, two, three, four, five, six, seven, eight, nine, or more times to parent A to produce selected backcross progeny plants comprising the desired trait of parent B and the physiological and morphological characteristics of parent A. Step (c) may or may not be repeated and included between the backcrosses of step (d).

The selection of a suitable recurrent parent is an important step for a successful backcrossing procedure. The goal of a backcross protocol is to alter or substitute one or more trait(s) or characteristic(s) in the original inbred parental line in order to find it then in the hybrid made thereof. To accomplish this, a gene or genes of the recurrent inbred is modified or substituted with the desired gene or genes from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait(s) to the plant. The exact backcrossing protocol will depend on the characteristic(s) or trait(s) being altered to determine an appropriate testing protocol. Although backcrossing methods are simplified when the characteristic being transferred is a single gene and dominant allele, multiple genes and recessive allele(s) may also be transferred and therefore, backcross breeding is by no means restricted to character(s) governed by one or a few genes. In fact the number of genes might be less important that the identification of the character(s) in the segregating population. In this instance it may then be necessary to introduce a test of the progeny to determine if the desired characteristic(s) has been successfully transferred. Such tests encompass visual inspection, simple crossing, but also follow up of the characteristic(s) through genetically associated markers and molecular assisted breeding tools. For example, selection of progeny containing the transferred trait is done by direct selection, visual inspection for a trait associated with a dominant allele, while the selection of progeny for a trait that is transferred via a recessive allele, such as the waxy starch characteristic in corn, require selfing the progeny to determine which plant carry the recessive allele(s).

Many single gene traits have been identified that are not regularly selected for in the development of a new parental inbred of a hybrid lettuce plant according to the disclosure but that can be improved by backcrossing techniques. These genes are generally inherited through the nucleus.

In 1981, the backcross method of breeding counted for 17% of the total breeding effort for inbred line development in the United States, accordingly to, Hallauer, A. R. et al. (1988) "Corn Breeding" Corn and Corn Improvement, No. 18, pp. 463-481.

The backcross breeding method provides a precise way of improving varieties that excel in a large number of attributes but are deficient in a few characteristics. (Page 150 of the Pr. R. W. Allard's 1960 book, published by John Wiley & Sons, Inc, Principles of Plant Breeding). The method makes use of a series of backcrosses to the variety to be improved during which the character or the characters in which improvement is sought is maintained by selection. At the end of the backcrossing the gene or genes being transferred unlike all other genes, will be heterozygous. Selfing after the last backcross produces homozygosity for this gene pair(s) and, coupled with selection, will result in a parental line of a hybrid variety with exactly the adaptation, yielding ability and quality characteristics of the recurrent parent but superior to that parent in the particular characteristic(s) for which the improvement program was undertaken. Therefore, this method provides the plant breeder with a high degree of genetic control of his work.

The method is scientifically exact because the morphological and agricultural features of the improved variety could be described in advance and because the same variety could, if it were desired, be bred a second time by retracing the same steps (Briggs, "Breeding wheats resistant to bunt by the backcross method", 1930 Jour. Amer. Soc. Agron., 22: 289-244).

Backcrossing is a powerful mechanism for achieving homozygosity and any population obtained by backcrossing must rapidly converge on the genotype of the recurrent parent. When backcrossing is made the basis of a plant breeding program, the genotype of the recurrent parent will be modified only with regards to genes being transferred, which are maintained in the population by selection.

Successful backcrosses are, for example, the transfer of stem rust resistance from 'Hope' wheat to 'Bart wheat' and even pursuing the backcrosses with the transfer of bunt resistance to create 'Bart 38', having both resistances. Also highlighted by Allard is the successful transfer of mildew, leaf spot and wilt resistances in California Common alfalfa to create 'Caliverde'. This new 'Caliverde' variety produced through the backcross process is indistinguishable from California Common except for its resistance to the three named diseases.

One of the advantages of the backcross method is that the breeding program can be carried out in almost every environment that will allow the development of the character being transferred.

The backcross technique is not only desirable when breeding for disease resistance but also for the adjustment of morphological characters, color characteristics and simply inherited quantitative characters such as earliness, plant height and seed size and shape.

iii Single-Seed Descent and Multiple Seed Procedures

The single-seed descent procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

In a multiple-seed procedure, breeders commonly harvest one or more flower containing seed from each plant in a population and blend them together to form a bulk seed lot. Part of the bulked seed is used to plant the next generation and part is put in reserve. The procedure has been referred to as modified single-seed descent or the bulk technique.

The multiple-seed procedure has been used to save labor at harvest. It is considerably faster than removing one seed from each flower by hand for the single seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., R. W. Allard, 1960, Principles of Plant Breeding, John Wiley and Son, pp. 115-161; N. W. Simmonds, 1979, Principles of Crop Improvement, Longman Group Limited; W. R. Fehr, 1987, Principles of Crop Development, Macmillan Publishing Co.; N. F. Jensen, 1988, Plant Breeding Methodology, John Wiley & Sons).

iv Open-Pollinated Populations

The improvement of open-pollinated populations of such crops as rye, maize and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity.

Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement.

First, there is the situation in which a population is changed en masse by a chosen selection procedure. The outcome is an improved population that is indefinitely propagable by random-mating within itself in isolation.

Second, the synthetic variety attains the same end result as population improvement, but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

A) Mass Selection

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

B) Synthetics

A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or more cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enters a synthetic varies widely. In practice, numbers of parental lines range from 10 to several hundred, with 100-200 being the average. Broad based synthetics formed from 100 or more clones would be expected to be more stable during seed multiplication than narrow based synthetics.

v. Hybrids

A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the F1 progeny. A double-cross hybrid is produced from four inbred lines crossed in pairs (A×B and C×D) and then the two F1 hybrids are crossed again (A×B)×(C×D). Much of the hybrid vigor and uniformity exhibited by F1 hybrids is lost in the next generation (F2). Consequently, seed from F2 hybrid varieties is not used for planting stock.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

vi. Bulk Segregation Analysis (BSA)

BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markers in specific genomic regions by using segregating populations. *Proceedings of the National Academy of Sciences, USA*, 99:9828-9832) and Quarrie et al. (Quarrie et al., 1999, *Journal of Experimental Botany*, 50(337):1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to virus), and the other from the individuals having reversed phenotype (e.g., susceptible to virus), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs, SNPs or SSRs). Markers linked to the phenotype can be identified and used for breeding or QTL mapping.

vii. Hand-Pollination Method

Hand pollination describes the crossing of plants via the deliberate fertilization of female ovules with pollen from a desired male parent plant. In some embodiments the donor or recipient female parent and the donor or recipient male parent line are planted in the same field. In some embodiments the donor or recipient female parent and the donor or recipient male parent line are planted in the same greenhouse. The inbred male parent can be planted earlier than the female parent to ensure adequate pollen supply at the pollination time. In some embodiments, the male parent and female parent can be planted at a ratio of 1 male parent to 4-10 female parents. Pollination is started when the female parent flower is ready to be fertilized. Female flower buds that are ready to open in the following days are identified, covered with paper cups or small paper bags that prevent bee or any other insect from visiting the female flowers, and marked with any kind of material that can be easily seen the next morning. The male flowers of the male parent are collected in the early morning before they are open and visited by pollinating insects. The covered female flowers of the female parent, which have opened, are un-covered and pollinated with the collected fresh male flowers of the male parent, starting as soon as the male flower sheds pollen. The pollinated female flowers are again covered after pollination to prevent bees and any other insects visit. The pollinated female flowers are also marked. The marked flowers are harvested. In some embodiments, the male pollen used for fertilization has been previously collected and stored.

vii. Bee-Pollination Method

Using the bee-pollination method, the parent plants are usually planted within close proximity. In some embodiments more female plants are planted to allow for a greater production of seed. Insects are placed in the field or greenhouses for transfer of pollen from the male parent to the female flowers of the female parent.

ix. Targeting Induced Local Lesions in Genomes (TILLING)

Breeding schemes of the present application can include crosses with TILLING® plant cultivars. TILLING® is a method in molecular biology that allows directed identification of mutations in a specific gene. TILLING® was introduced in 2000, using the model plant *Arabidopsis thaliana*. TILLING® has since been used as a reverse genetics method in other organisms such as zebrafish, corn, wheat, rice, soybean, tomato and lettuce.

The method combines a standard and efficient technique of mutagenesis with a chemical mutagen (e.g., Ethyl methanesulfonate (EMS)) with a sensitive DNA screening-technique that identifies single base mutations (also called point mutations) in a target gene. EcoTILLING is a method that uses TILLING® techniques to look for natural mutations in individuals, usually for population genetics analysis (see Comai, et al., 2003 The Plant Journal 37, 778-786; Gilchrist et al. 2006 Mol. Ecol. 15, 1367-1378; Mejlhede et al. 2006 Plant Breeding 125, 461-467; Nieto et al. 2007 BMC Plant Biology 7, 34-42, each of which is incorporated by reference hereby for all purposes). DEcoTILLING is a modification of TILLING® and EcoTILLING which uses an inexpensive method to identify fragments (Garvin et al., 2007, DEcoTILLING: An inexpensive method for SNP discovery that reduces ascertainment bias. Molecular Ecology Notes 7, 735-746).

The TILLING® method relies on the formation of heteroduplexes that are formed when multiple alleles (which could be from a heterozygote or a pool of multiple homozygotes and heterozygotes) are amplified in a PCR, heated, and then slowly cooled. As DNA bases are not pairing at the mismatch of the two DNA strands (the induced mutation in TILLING® or the natural mutation or SNP in EcoTILLING), they provoke shape change in the double strand DNA fragment which is then cleaved by single stranded nucleases. The products are then separated by size on several different platforms.

More detailed description on methods and compositions on TILLING® can be found in U.S. Pat. No. 5,994,075, US 2004/0053236 A1, WO 2005/055704, and WO 2005/048692, each of which is hereby incorporated by reference for all purposes.

Thus in some embodiments, the breeding methods of the present disclosure include breeding with one or more TILLING plant lines with one or more identified mutations.

x. Mutation Breeding

Mutation breeding is another method of introducing new variation and subsequent traits into plants. Mutations that occur spontaneously or are artificially induced can be useful sources of variability for a plant breeder. The goal of artificial mutagenesis is to increase the rate of mutation for a desired characteristic. Mutation rates can be increased by many different means or mutating agents including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in W. R. Fehr, 1993, Principles of Cultivar Development, Macmillan Publishing Co.

New breeding techniques such as the ones involving the uses of Zinc Finger Nucleases or oligonucleotide directed mutagenesis shall also be used to generate genetic variability and introduce new traits into varieties.

xi. Double Haploids and Chromosome Doubling

One way to obtain homozygous plants without the need to cross two parental lines followed by a long selection of the segregating progeny, and/or multiple backcrossings is to produce haploids and then double the chromosomes to form doubled haploids. Haploid plants can occur spontaneously, or may be artificially induced via chemical treatments or by crossing plants with inducer lines (Seymour et al. 2012, PNAS vol 109, pg 4227-4232; Zhang et al., 2008 Plant Cell Rep. December 27(12) 1851-60). The production of haploid progeny can occur via a variety of mechanisms which can affect the distribution of chromosomes during gamete formation. The chromosome complements of haploids sometimes double spontaneously to produce homozygous doubled haploids (DHs). Mixoploids, which are plants which contain cells having different ploidies, can sometimes arise and may represent plants that are undergoing chromosome doubling so as to spontaneously produce doubled haploid tissues, organs, shoots, floral parts or plants. Another common technique is to induce the formation of double haploid plants with a chromosome doubling treatment such as colchicine (El-Hennawy et al., 2011 Vol 56, issue 2 pg 63-72; Doubled Haploid Production in Crop Plants 2003 edited by Maluszynski ISBN 1-4020-1544-5). The production of doubled haploid plants yields highly uniform cultivars and is especially desirable as an alternative to sexual inbreeding of longer-generation crops. By producing doubled haploid progeny, the number of possible gene combinations for inherited traits is more manageable. Thus, an efficient doubled haploid technology can significantly reduce the time and the cost of inbred and cultivar development.

xii. Protoplast Fusion

In another method for breeding plants, protoplast fusion can also be used for the transfer of trait-conferring genomic material from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell that may even be obtained with plant species that cannot be interbred in nature is tissue cultured into a hybrid plant exhibiting the desirable combination of traits.

xiii. Embryo Rescue

Alternatively, embryo rescue may be employed in the transfer of resistance-conferring genomic material from a donor plant to a recipient plant. Embryo rescue can be used as a procedure to isolate embryo's from crosses wherein plants fail to produce viable seed. In this process, the fertilized ovary or immature seed of a plant is tissue cultured to create new plants (see Pierik, 1999, *In vitro culture of higher plants*, Springer, ISBN 079235267x, 9780792352679, which is incorporated herein by reference in its entirety).

Breeding Evaluation

Each breeding program can include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested per se and in hybrid combination and compared to appropriate standards in environments representative of the commercial target area(s). The best lines are candidates for use as parents in new commercial cultivars; those still deficient in a few traits may be used as parents to produce new populations for further selection.

In one embodiment, the plants are selected on the basis of one or more phenotypic traits. Skilled persons will readily appreciate that such traits include any observable characteristic of the plant, including for example growth rate, height, weight, color, taste, smell, changes in the production of one or more compounds by the plant (including for example, metabolites, proteins, drugs, carbohydrates, oils, and any other compounds).

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

It should be appreciated that in certain embodiments, plants may be selected based on the absence, suppression or inhibition of a certain feature or trait (such as an undesirable feature or trait) as opposed to the presence of a certain feature or trait (such as a desirable feature or trait).

Selecting plants based on genotypic information is also envisaged (for example, including the pattern of plant gene expression, genotype, or presence of genetic markers). Where the presence of one or more genetic marker is assessed, the one or more marker may already be known and/or associated with a particular characteristic of a plant; for example, a marker or markers may be associated with an increased growth rate or metabolite profile. This information could be used in combination with assessment based on other characteristics in a method of the disclosure to select for a combination of different plant characteristics that may be desirable. Such techniques may be used to identify novel quantitative trait loci (QTLs). By way of example, plants may be selected based on growth rate, size (including but not limited to weight, height, leaf size, stem size, branching pattern, or the size of any part of the plant), general health, survival, tolerance to adverse physical environments and/or any other characteristic, as described herein before.

Further non-limiting examples include selecting plants based on: speed of seed germination; quantity of biomass produced; increased root, and/or leaf/shoot growth that leads to an increased yield (herbage or grain or fiber or oil, or fruit or leaves) or biomass production; effects on plant growth that results in an increased seed yield for a crop; effects on plant growth which result in an increased yield; effects on plant growth that lead to an increased resistance or tolerance to disease including fungal, viral or bacterial diseases, to *mycoplasma* or to pests such as insects, mites or nematodes in which damage is measured by decreased foliar symptoms such as the incidence of bacterial or fungal lesions, or area of damaged foliage or reduction in the numbers of nematode cysts or galls on plant roots, or improvements in plant yield in the presence of such plant pests and diseases; effects on plant growth that lead to increased metabolite yields; effects on plant growth that lead to improved aesthetic appeal which may be particularly important in plants grown for their form, color or taste, for example the color intensity of *Justicia* leaves, or the taste of said leaves.

Molecular Breeding Evaluation Techniques

Selection of plants based on phenotypic or genotypic information may be performed using techniques such as, but not limited to: high through-put screening of chemical components of plant origin, sequencing techniques including high through-put sequencing of genetic material, differential display techniques (including DDRT-PCR, and DD-PCR), nucleic acid microarray techniques, RNA-seq (transcriptome sequencing), qRTPCR (quantitative real time PCR).

In one embodiment, the evaluating step of a plant breeding program involves the identification of desirable traits in progeny plants. Progeny plants can be grown in, or exposed to conditions designed to emphasize a particular trait (e.g. drought conditions for drought tolerance, lower temperatures for freezing tolerant traits). Progeny plants with the highest scores for a particular trait may be used for subsequent breeding steps.

In some embodiments, plants selected from the evaluation step can exhibit a 1%, 5%, 10%, 15%, 20%, 25%, 30%, 35%, 40%, 45%, 50%, 55%, 60%, 65%, 70%, 75%, 80%, 85%, 90%, 95%, 100%, 120% or more improvement in a particular plant trait compared to a control plant.

In other embodiments, the evaluating step of plant breeding comprises one or more molecular biological tests for genes or other markers. For example, the molecular biological test can involve probe hybridization and/or amplification of nucleic acid (e.g., measuring nucleic acid density by Northern or Southern hybridization, PCR) and/or immunological detection (e.g., measuring protein density, such as precipitation and agglutination tests, ELISA (e.g., Lateral Flow test or DAS-ELISA), Western blot, immune labeling, immunosorbent electron microscopy (ISEM), and/or dot blot).

The procedure to perform a nucleic acid hybridization, an amplification of nucleic acid (e.g., PCR, RT-PCR) or an immunological detection (e.g., precipitation and agglutination tests, ELISA (e.g., Lateral Flow test or DAS-ELISA), Western blot, RIA, immunogold or immunofluorescent labeling, immunosorbent electron microscopy (ISEM), and/or dot blot tests) are performed as described elsewhere herein and well-known by one skilled in the art.

In one embodiment, the evaluating step comprises PCR (semi-quantitative or quantitative), wherein primers are used to amplify one or more nucleic acid sequences of a desirable gene, or a nucleic acid associated with said gene or QTL or a desirable trait (e.g., a co-segregating nucleic acid, or other marker).

In another embodiment, the evaluating step comprises immunological detection (e.g., precipitation and agglutination tests, ELISA (e.g., Lateral Flow test or DAS-ELISA), Western blot, RIA, immuno labeling (gold, fluorescent, or other detectable marker), immunosorbent electron microscopy (ISEM), and/or dot blot), wherein one or more gene or marker-specific antibodies are used to detect one or more desirable proteins. In one embodiment, said specific antibody is selected from the group consisting of polyclonal antibodies, monoclonal antibodies, antibody fragments, and combination thereof.

Reverse Transcription Polymerase Chain Reaction (RT-PCR) can be utilized in the present disclosure to determine expression of a gene to assist during the selection step of a breeding scheme. It is a variant of polymerase chain reaction (PCR), a laboratory technique commonly used in molecular biology to generate many copies of a DNA sequence, a process termed "amplification". In RT-PCR, however, RNA strand is first reverse transcribed into its DNA complement (complementary DNA, or cDNA) using the enzyme reverse transcriptase, and the resulting cDNA is amplified using traditional or real-time PCR.

RT-PCR utilizes a pair of primers, which are complementary to a defined sequence on each of the two strands of the mRNA. These primers are then extended by a DNA polymerase and a copy of the strand is made after each cycle, leading to logarithmic amplification.

RT-PCR includes three major steps. The first step is the reverse transcription (RT) where RNA is reverse transcribed to cDNA using a reverse transcriptase and primers. This step is very important in order to allow the performance of PCR since DNA polymerase can act only on DNA templates. The RT step can be performed either in the same tube with PCR (one-step PCR) or in a separate one (two-step PCR) using a temperature between 40° C. and 50° C., depending on the properties of the reverse transcriptase used.

The next step involves the denaturation of the dsDNA at 95° C., so that the two strands separate and the primers can bind again at lower temperatures and begin a new chain reaction. Then, the temperature is decreased until it reaches the annealing temperature which can vary depending on the set of primers used, their concentration, the probe and its concentration (if used), and the cation concentration. The main consideration, of course, when choosing the optimal annealing temperature is the melting temperature (Tm) of the primers and probes (if used). The annealing temperature chosen for a PCR depends directly on length and composition of the primers. This is the result of the difference of hydrogen bonds between A-T (2 bonds) and G-C (3 bonds). An annealing temperature about 5 degrees below the lowest Tm of the pair of primers is usually used.

The final step of PCR amplification is the DNA extension from the primers which is done by the thermostable Taq DNA polymerase usually at 72° C., which is the optimal temperature for the polymerase to work. The length of the incubation at each temperature, the temperature alterations and the number of cycles are controlled by a programmable thermal cycler. The analysis of the PCR products depends on the type of PCR applied. If a conventional PCR is used, the PCR product is detected using for example agarose gel electrophoresis or other polymer gel like polyacrylamide gels and ethidium bromide (or other nucleic acid staining).

Conventional RT-PCR is a time-consuming technique with important limitations when compared to real time PCR techniques. Furthermore, the specificity of the assay is mainly determined by the primers, which can give false-positive results. However, the most important issue concerning conventional RT-PCR is the fact that it is a semi or even a low quantitative technique, where the amplicon can be visualized only after the amplification ends.

Real time RT-PCR provides a method where the amplicons can be visualized as the amplification progresses using a fluorescent reporter molecule. There are three major kinds of fluorescent reporters used in real time RT-PCR, general nonspecific DNA Binding Dyes such as SYBR Green I, TaqMan Probes and Molecular Beacons (including Scorpions).

The real time PCR thermal cycler has a fluorescence detection threshold, below which it cannot discriminate the difference between amplification generated signal and background noise. On the other hand, the fluorescence increases as the amplification progresses and the instrument performs data acquisition during the annealing step of each cycle. The number of amplicons will reach the detection baseline after a specific cycle, which depends on the initial concentration of the target DNA sequence. The cycle at which the instrument can discriminate the amplification generated fluorescence from the background noise is called the threshold cycle (Ct). The higher is the initial DNA concentration, the lower its Ct will be.

Other forms of nucleic acid detection can include next generation sequencing methods such as DNA SEQ or RNA SEQ using any known sequencing platform including, but not limited to: Roche 454, Solexa Genome Analyzer, AB SOLiD, Illumina GA/HiSeq, Ion PGM, Mi Seq, among others (Liu et al., 2012 Journal of Biomedicine and Biotechnology Volume 2012 ID 251364; Franca et al., 2002 Quarterly Reviews of Biophysics 35 pg. 169-200; Mardis 2008 Genomics and Human Genetics vol 9 pg 387-402).

In other embodiments, nucleic acids may be detected with other high throughput hybridization technologies including microarrays, gene chips, LNA probes, nanoStrings, and fluorescence polarization detection among others.

In some embodiments, detection of markers can be achieved at an early stage of plant growth by harvesting a small tissue sample (e.g., branch, or leaf disk). This approach is preferable when working with large populations as it allows breeders to weed out undesirable progeny at an early stage and conserve growth space and resources for progeny which show more promise. In some embodiments the detection of markers is automated, such that the detection and storage of marker data is handled by a machine. Recent advances in robotics have also led to full service analysis tools capable of handling nucleic acid/protein marker extractions, detection, storage and analysis.

Quantitative Trait Loci

Breeding schemes of the present application can include crosses between donor and recipient plants. In some embodiments said donor plants contain a gene or genes of interest which may confer the plant with a desirable phenotype. The recipient line can be an elite line or cultivar having certain favorite traits such for commercial production. In one embodiment, the elite line may contain other genes that also impart said line with the desired phenotype. When crossed together, the donor and recipient plant may create a progeny plant with combined desirable loci which may provide quantitatively additive effect of a particular characteristic. In that case, QTL mapping can be involved to facilitate the breeding process.

A QTL (quantitative trait locus) mapping can be applied to determine the parts of the donor plant's genome conferring the desirable phenotype, and facilitate the breeding methods. Inheritance of quantitative traits or polygenic inheritance refers to the inheritance of a phenotypic characteristic that varies in degree and can be attributed to the interactions between two or more genes and their environment. Though not necessarily genes themselves, quantitative trait loci (QTLs) are stretches of DNA that are closely linked to the genes that underlie the trait in question. QTLs can be molecularly identified to help map regions of the genome that contain genes involved in specifying a quantitative trait. This can be an early step in identifying and sequencing these genes.

Typically, QTLs underlie continuous traits (those traits that vary continuously, e.g. yield, height, level of resistance to virus, etc.) as opposed to discrete traits (traits that have two or several character values, e.g. smooth vs. wrinkled peas used by Mendel in his experiments). Moreover, a single phenotypic trait is usually determined by many genes. Consequently, many QTLs are associated with a single trait.

A quantitative trait locus (QTL) is a region of DNA that is associated with a particular phenotypic trait. Knowing the number of QTLs that explains variation in the phenotypic trait tells about the genetic architecture of a trait. It may tell that a trait is controlled by many genes of small effect, or by a few genes of large effect or by a several genes of small effect and few genes of larger effect.

Another use of QTLs is to identify candidate genes underlying a trait. Once a region of DNA is identified as contributing to a phenotype, it can be sequenced. The DNA sequence of any genes in this region can then be compared to a database of DNA for genes whose function is already known.

In a recent development, classical QTL analyses are combined with gene expression profiling i.e. by DNA microarrays. Such expression QTLs (e-QTLs) describes cis- and trans-controlling elements for the expression of often disease-associated genes. Observed epistatic effects have been found beneficial to identify the gene responsible by a cross-validation of genes within the interacting loci with metabolic pathway- and scientific literature databases.

QTL mapping is the statistical study of the alleles that occur in a locus and the phenotypes (physical forms or traits) that they produce (see, Meksem and Kahl, *The handbook of plant genome mapping: genetic and physical mapping*, 2005. Wiley-VCH, ISBN 3527311165,9783527311163). Because most traits of interest are governed by more than one gene, defining and studying the entire locus of genes related to a trait gives hope of understanding what effect the genotype of an individual might have in the real world.

Statistical analysis is required to demonstrate that different genes interact with one another and to determine whether they produce a significant effect on the phenotype. QTLs identify a particular region of the genome as containing one or several genes, i.e. a cluster of genes that is associated with the trait being assayed or measured. They are shown as intervals across a chromosome, where the probability of association is plotted for each marker used in the mapping experiment.

To begin, a set of genetic markers must be developed for the species in question. A marker is an identifiable region of variable DNA. Biologists are interested in understanding the genetic basis of phenotypes (physical traits). The aim is to find a marker that is significantly more likely to co-occur with the trait than expected by chance, that is, a marker that has a statistical association with the trait. Ideally, they would be able to find the specific gene or genes in question, but this is a long and difficult undertaking. Instead, they can more readily find regions of DNA that are very close to the genes in question. When a QTL is found, it is often not the actual gene underlying the phenotypic trait, but rather a region of DNA that is closely linked with the gene.

For organisms whose genomes are known, one might now try to exclude genes in the identified region whose function is known with some certainty not to be connected with the trait in question. If the genome is not available, it may be an option to sequence the identified region and determine the putative functions of genes by their similarity to genes with known function, usually in other genomes. This can be done using BLAST, an online tool that allows users to enter a primary sequence and search for similar sequences within the BLAST database of genes from various organisms.

Another interest of statistical geneticists using QTL mapping is to determine the complexity of the genetic architecture underlying a phenotypic trait. For example, they may be interested in knowing whether a phenotype is shaped by many independent loci, or by a few loci, and how do those loci interact. This can provide information on how the phenotype may be evolving.

Molecular markers are used for the visualization of differences in nucleic acid sequences. This visualization is possible due to DNA-DNA hybridization techniques (RFLP) and/or due to techniques using the polymerase chain reaction (e.g. STS, SNPs, microsatellites, AFLP). All differences between two parental genotypes will segregate in a mapping population based on the cross of these parental genotypes. The segregation of the different markers may be compared and recombination frequencies can be calculated. The recombination frequencies of molecular markers on different chromosomes are generally 50%. Between molecular markers located on the same chromosome the recombination frequency depends on the distance between the markers. A low recombination frequency usually corresponds to a low distance between markers on a chromosome. Comparing all recombination frequencies will result in the most logical order of the molecular markers on the chromosomes. This most logical order can be depicted in a linkage map (Paterson, 1996, Genome Mapping in Plants. R. G. Landes, Austin.). A group of adjacent or contiguous markers on the linkage map that is associated to a reduced disease incidence and/or a reduced lesion growth rate pinpoints the position of a QTL.

The nucleic acid sequence of a QTL may be determined by methods known to the skilled person. For instance, a nucleic acid sequence comprising said QTL or a resistance-conferring part thereof may be isolated from a donor plant by fragmenting the genome of said plant and selecting those fragments harboring one or more markers indicative of said QTL. Subsequently, or alternatively, the marker sequences (or parts thereof) indicative of said QTL may be used as (PCR) amplification primers, in order to amplify a nucleic acid sequence comprising said QTL from a genomic nucleic acid sample or a genome fragment obtained from said plant. The amplified sequence may then be purified in order to obtain the isolated QTL. The nucleotide sequence of the QTL, and/or of any additional markers comprised therein, may then be obtained by standard sequencing methods.

One or more such QTLs associated with a desirable trait in a donor plant can be transferred to a recipient plant to incorporate the desirable trait into progeny plants by transferring and/or breeding methods.

In one embodiment, an advanced backcross QTL analysis (AB-QTL) is used to discover the nucleotide sequence or the QTLs responsible for the resistance of a plant. Such method was proposed by Tanksley and Nelson in 1996 (Tanksley and Nelson, 1996, Advanced backcross QTL analysis: a method for simultaneous discovery and transfer of valuable QTL from un-adapted germplasm into elite breeding lines. *Theor Appl Genet* 92:191-203) as a new breeding method that integrates the process of QTL discovery with variety development, by simultaneously identifying and transferring useful QTL alleles from un-adapted (e.g., land races, wild species) to elite germplasm, thus broadening the genetic diversity available for breeding. AB-QTL strategy was initially developed and tested in tomato, and has been adapted for use in other crops including rice, maize, wheat, pepper, barley, and bean. Once favorable QTL alleles are detected, only a few additional marker-assisted generations are required to generate near isogenic lines (NILs) or introgression lines (ILs) that can be field tested in order to confirm the QTL effect and subsequently used for variety development.

Isogenic lines in which favorable QTL alleles have been fixed can be generated by systematic backcrossing and introgressing of marker-defined donor segments in the recurrent parent background. These isogenic lines are referred to as near isogenic lines (NILs), introgression lines (ILs), backcross inbred lines (BILs), backcross recombinant inbred lines (BCRIL), recombinant chromosome substitution lines (RCSLs), chromosome segment substitution lines (CSSLs), and stepped aligned inbred recombinant strains (STAIRSs). An introgression line in plant molecular biology is a line of a crop species that contains genetic material derived from a similar species. ILs represent NILs with relatively large average introgression length, while BILs and BCRILs are backcross populations generally containing multiple donor introgressions per line. As used herein, the term "introgression lines or ILs" refers to plant lines containing a single marker defined homozygous donor segment, and the term "pre-ILs" refers to lines which still contain multiple homozygous and/or heterozygous donor segments.

To enhance the rate of progress of introgression breeding, a genetic infrastructure of exotic libraries can be developed. Such an exotic library comprises a set of introgression lines, each of which has a single, possibly homozygous, marker-defined chromosomal segment that originates from a donor exotic parent, in an otherwise homogenous elite genetic background, so that the entire donor genome would be represented in a set of introgression lines. A collection of such introgression lines is referred as libraries of introgression lines or IL libraries (ILLs). The lines of an ILL cover usually the complete genome of the donor, or the part of interest. Introgression lines allow the study of quantitative trait loci, but also the creation of new varieties by introducing exotic traits. High resolution mapping of QTL using ILLs enable breeders to assess whether the effect on the phenotype is due to a single QTL or to several tightly linked QTL affecting the same trait. In addition, sub-ILs can be developed to discover molecular markers which are more tightly linked to the QTL of interest, which can be used for marker-assisted breeding (MAB). Multiple introgression lines can be developed when the introgression of a single QTL is not sufficient to result in a substantial improvement in agriculturally important traits (Gur and Zamir, Unused natural variation can lift yield barriers in plant breeding, 2004, *PLoS Biol.;* 2(10):e245).

Tissue Culture

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, leaves, stems, roots, root tips, anthers, pistils, meristematic cells, axillary buds, ovaries, seed coat, endosperm, hypocotyls, cotyledons and the like. Means for preparing and maintaining plant tissue culture are well known in the art. By way of example, a tissue culture comprising organs has been used to produce regenerated plants. U.S. Pat. Nos. 5,959,185, 5,973, 234, and 5,977,445 describe certain techniques, the disclosures of which are incorporated herein by reference. See also, e.g., Vinay and Afrox, Plant Tissue Culture, 2015, I.K. International Publishing House; Kavyashree and Gayatri, Plant Tissue Culture, 2015, Alpha Science Intl Ltd.; and Michael A. Dirr, The Reference Manual of Woody Plant Propagation: From Seed to Tissue Culture, Second Edition, 2006, Timber Press.

Tissue culture of *Justicia* can be used for the in vitro regeneration of *Justicia* plants. Standard plant tissue cultures methods and regeneration of plants therefrom are well known in the art. Thus, another aspect of this disclosure is to provide cells which upon growth and differentiation produce *Justicia* plants. In some embodiments, such tissue culture methods can be used to produce regenerated plants from cells and tissues of the 'Befu' cultivar, wherein such regenerated plants have all of the physiological and morphological characteristics of 'Befu.'

EXAMPLES

The foregoing examples of the related art and limitations related therewith are intended to be illustrative and not exclusive. Other limitations of the related art will become apparent to those of skill in the art upon a reading of the specification.

Example 1—Discovery of 'Befu' in a Cultivated Area

The plants of the present disclosure were discovered growing in a cultivated area on private land in Orlando, Fla., U.S.A. The parentage of the discovered plants is unknown. Possible unconfirmed origin of original plants grown in this cultivated area may have been from Cameroon.

Example 2—Identification of New *Justicia* Species Via DNA Analysis

A tissue sample, consisting of photosynthetic leaf material, of the plant of the present disclosure was preserved by silica gel desiccation. A voucher specimen (see voucher data below) to document the plant from which the sample was taken was collected, dried, and deposited in the US National Herbarium (Smithsonian Institution).

Voucher Specimen: *Justicia* sp. (Acanthaceae). Herb to 40 cm in height, leaves opposite, green with red ring at base of petiole, and no Flowers. DNA barcode voucher was taken from plant in cultivation in Orlando, Fla.; possible but not confirmed origin in Cameroon.

DNA was extracted from the silica-dried sample using a CTAB extraction method and stored at 80° C. Routine PCR was employed and primers for each marker followed Kress et al. (2010). Cycle sequencing protocols were the same for all markers. Following cycle sequencing, products are purified on a column of sephadex G50 in Millipore Multi-Screen 96-well plates and sequence reactions read on an ABI 3730. Forward and reverse sequences were assembled and aligned using Geneious Pro 4.6, TRANSALIGN, and Muscle depending on the DNA barcode marker. All DNA barcode sequences have been submitted to GenBank. DNA sequences from the unknown plant sample were compared against the plant DNA sequence data assembled in GenBank using the BLASTn algorithm (the core GenBank search engine) and default search parameters. In addition, the voucher specimen was compared to reference collections in the United States National Herbarium to confirm the DNA barcode identification.

Figure 11A:
FIGS. 11A and 11B provide a photograph of a 'Befu' plant grown in a cultivated area in Orlando, Fla., wherein the plant was asexually reproduced from a stem cutting from a parent plant.
Figure 11B:

To establish identity of the plant, DNA from photosynthetic leaf material of the plant was employed for DNA barcoding. DNA barcodes (including the markers rbcL, matK, and trnH-psbA) was generated by the protocol outlined by Kress et al. (2009, 2010) and Kress and Erickson (2012). BLAST results from the DNA barcode marker comparisons to GenBank sequence data established the plant to be of the genus *Justicia* in the family Acanthanceae. The DNA barcode sequence data however, were not able to identify a species for the plant, suggesting that the sample belonged to a new species of *Justicia*. The generic identity of the sample was further confirmed by a taxonomic specialist in the Department of Botany at the United States National Herbarium. *Justicia* includes over 600 species that are found in pantropical regions. These species are known to be evergreen perennials and shrubs with leaves that are characteristically petiolate, strongly veined, and with a margin that is usually entire (FIG. 11B). Based on these results, the 'Befu' plant was assigned to a new species named *Justicia sanguinis*.

Example 3—Plant Leaf Extract and Analyses

*Justicia* leaf sample was weighed and placed in known amount of purified water at ca. 80 degrees Fahrenheit and rotated to acquire extract while preserving blood components. The leaf sample was then removed from the liquid portion of the extract. The extract was then centrifuged at 12000 rpm until a pellet formed at the bottom of the vials. The centrifuged vials were then subjected to lyophilization in a LYO-0.2 freeze drier (Tofflon Science and Technology). The following freeze drying protocol was used: (1) freezing −50° C. for 3 hours with a cooling rate of 1° C./min; (2) primary drying, −50° C. for 60 hours at 3 Pa; and (3) secondary drying, 0° C. for 4 hours and 20° C. for 8 hours at 3 Pa. At the end of the process, the vials were rapidly stoppered under vacuum and stored for future use. To reconstitute liquid sample, the lyophilized powder was weighed and dissolved in measured quantity of sterile water to obtain concentration in mg/ml.

Figure 1B:
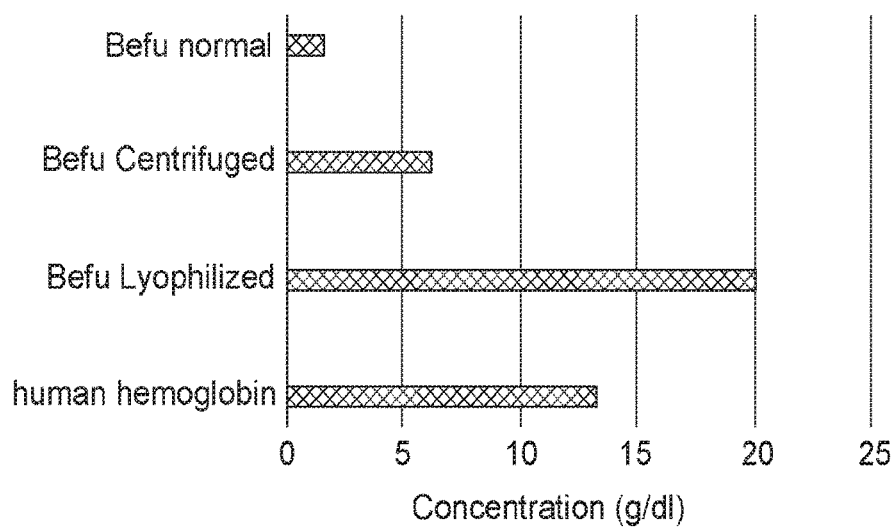
FIGS. 1B and 1C show the concentrations of hemoglobin levels for leaf extracts of the 'Befu' plant. Results are shown for lyophilized extract reconstituted in sterile water (Befu Lyophilized) as compared to human hemoglobin (human hemoglobin or Human Hemoglobin), centrifuged 'Befu' extract (Befu Centrifuged) and 'Befu' extract that has not been lyophilized or centrifuged (Befu normal).
Figure 1C:
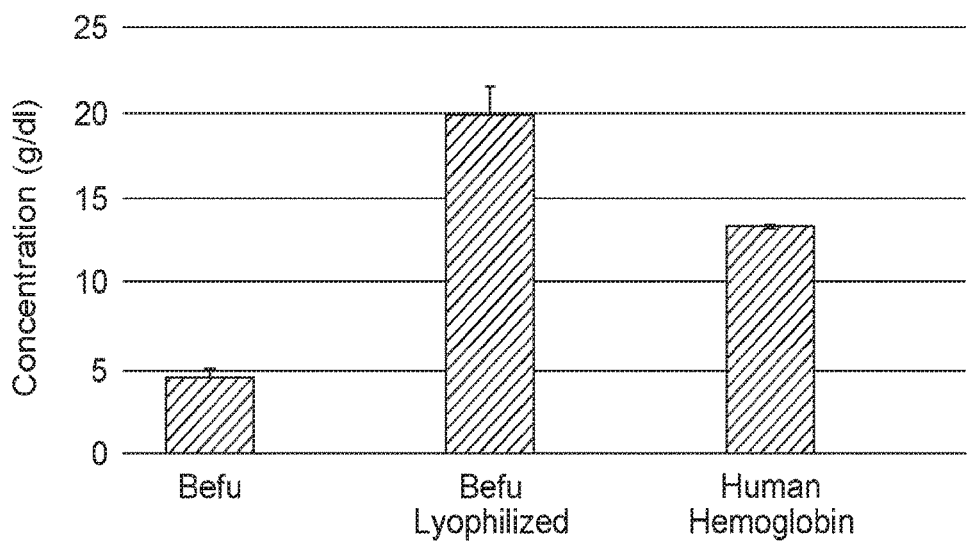

Befu plant extract (e.g. as pictured in FIG. 1A, and FIG. 2A) was tested for hemoglobin content via multiple methods. Results showed remarkably high hemoglobin concentrations in the extract (FIGS. 1B and 1C; FIG. 2C). Lyophilized leaf extracts reconstituted by dissolving in sterile water showed over 12 g/dl concentrations, comparable to solutions made of the same mass of lyophilized human hemoglobin (Sigma-Aldrich). Furthermore, FIG. 3 demonstrates higher hemoglobin concentration than other samples including beet root extract, water, and Acanthaceae plant from Puerto Rico.

Two separate human hemoglobin assay kits were used to assess the level of hemoglobin present in *Justicia* leaf extract in comparison to human hemoglobin as a control. First Cayman's hemoglobin assay was performed following the instructions of the manufacturer (Cayman Chemical). Materials included hemoglobin sample buffer, hemoglobin detector, hemoglobin standard, 96-Well solid plate, and 96-Well cover sheet. Briefly, 20 µl of prepared samples was added to three wells of the 96-well plate for each sample. 180 µl of hemoglobin detector was added to each sample well. The plate was then covered with the plate cover and incubated at room temperature for 15 minutes. The plate cover was then removed and the absorbance read at 575 nm. The absorbance versus concentration curve generated using standard sample was then used to determine the concentration of hemoglobin in the sample. Experiments were repeated for different dilutions. A second hemoglobin assay was performed per instructions of the manufacturer (Sigma-Aldrich) to further corroborate the findings. Testing with blood hemoglobin kits showed unusually high amounts of hemoglobin from the plant tissue which allows for modification to treat different blood disorders.

Example 4—Factors for Reconstitution and Preservation of 'Befu' Plant Extracts

Figure 4:
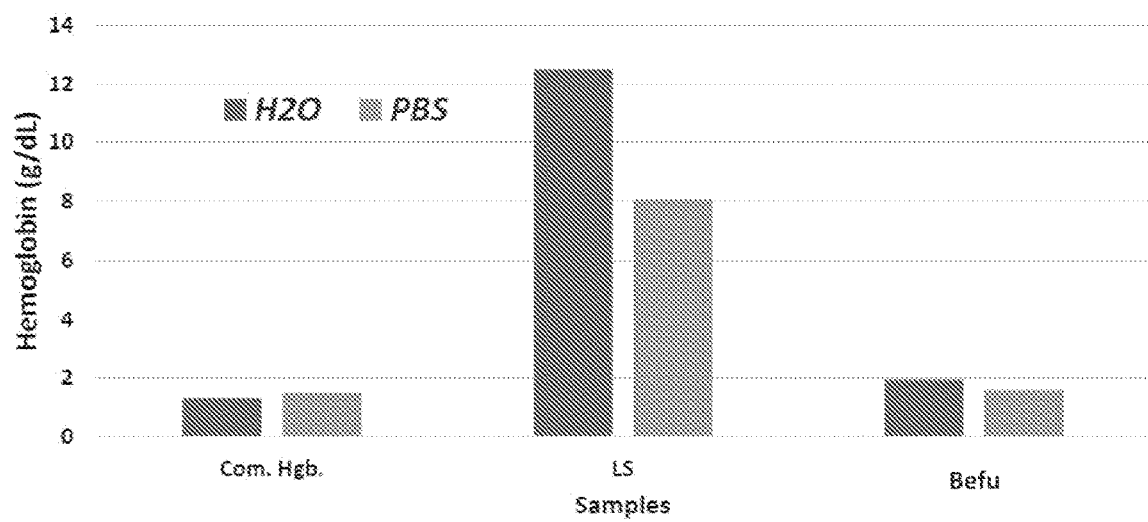
FIG. 4 shows the effect of media used for sample reconstitution. Samples were reconstituted in water and PBS to find optimizable media.
Figure 5A:
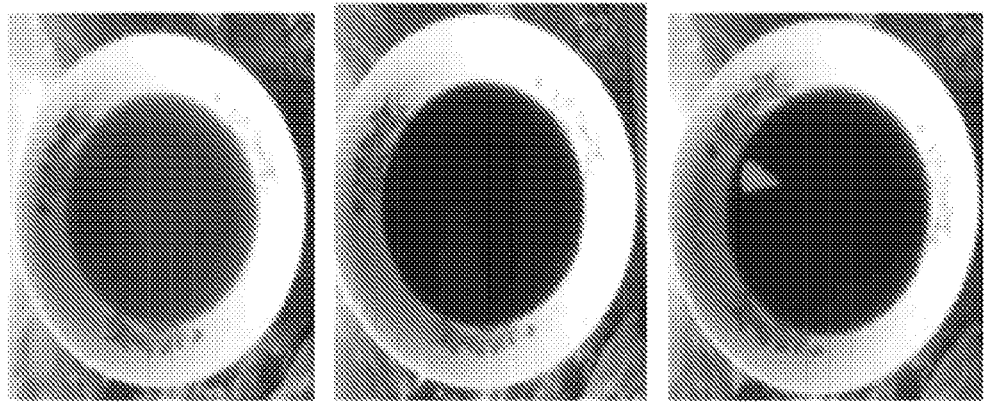
FIG. 5A shows a picture of new safe extract of different concentrations with methods that preserve the key components of blood from the leaf extract of 'Befu' plant.
Figure 5B:
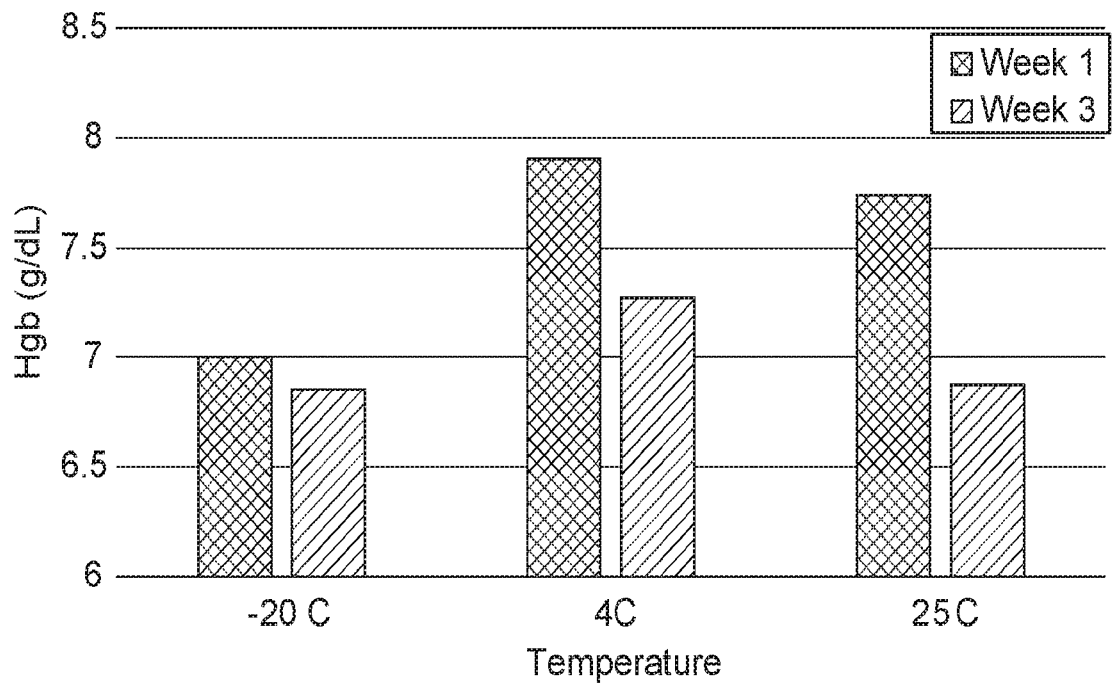
FIG. 5B illustrates results on hemoglobin preservation. The effect of time (1 week and 3 weeks) to hemoglobin preservation and stability are shown on 'Befu' extract samples at different temperatures.
Figure 6A:
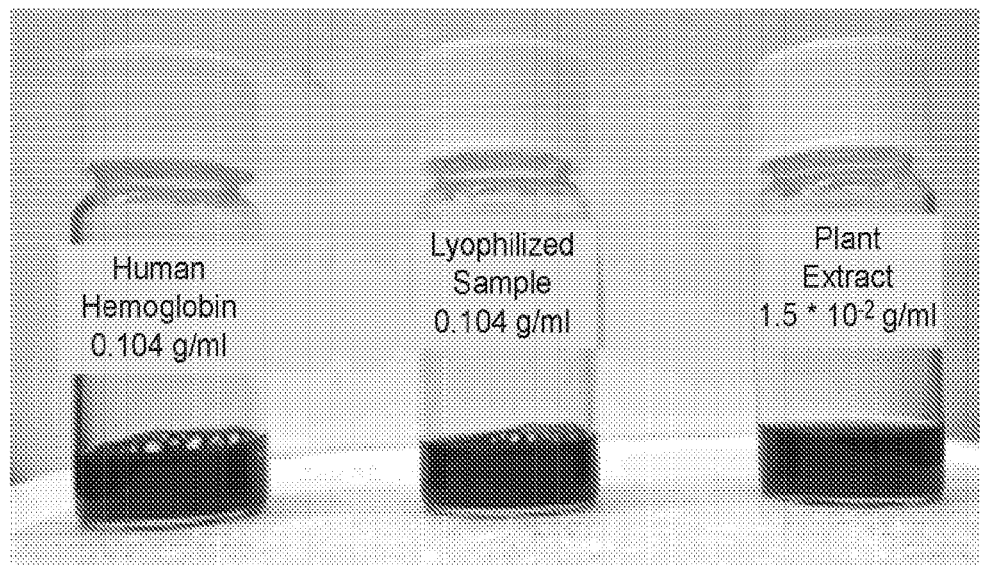
FIG. 6A provides a picture of samples of human hemoglobin, normal 'Befu' extract, and lyophilized 'Befu' extract for UV-VIS absorption spectroscopy analysis.
Figure 6B:
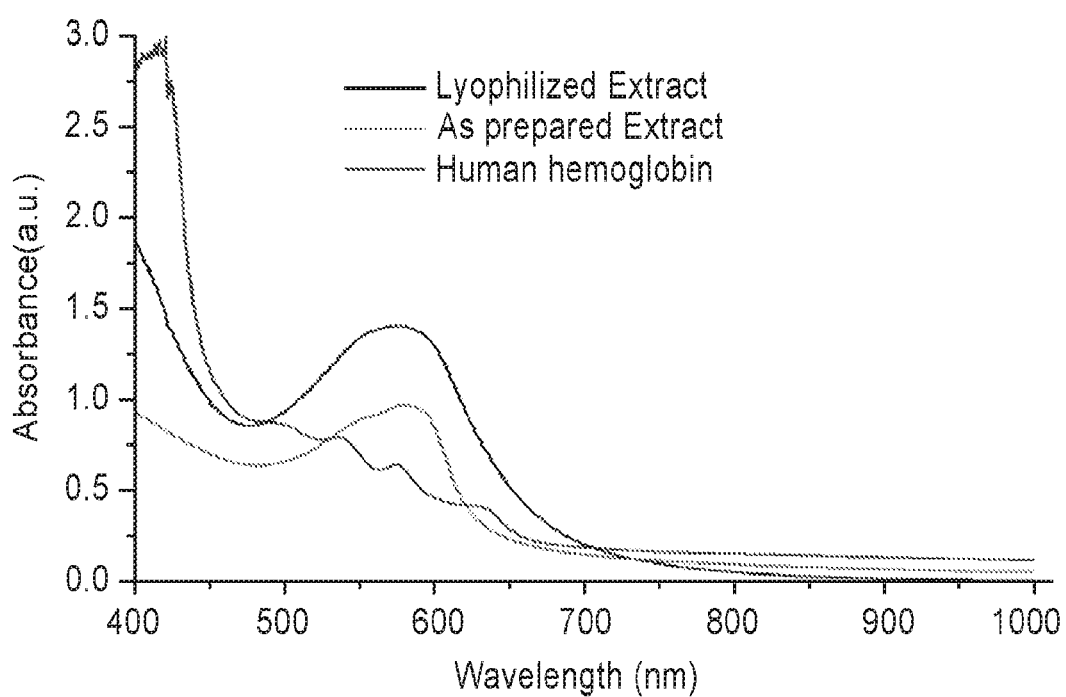
FIG. 6B shows UV-VIS absorption spectroscopy analysis results with absorption peaks verifying the presence of deoxyhemoglobin (a useful form of hemoglobin). Samples were compared with methemoglobin (commercial human hemoglobin from Sigma-Aldrich®).

To test whether medium affects hemoglobin reconstitution and find optimizable media, the lyophilized 'Befu' extract samples were reconstituted in water and Phosphate Buffered Solution (PBS). FIG. 4 shows the water solution is better reconstitution of hemoglobin than PBS solution. Also, to test how temperature affects hemoglobin stability over the time. FIG. 5B illustrates that the hemoglobin from the 'Befu' plant extracts shows no significant difference at 4° C. and 25° C. (room temperature), which indicates that hemoglobin from the 'Befu' plant extracts can be stored and preserved in room temperature. This suggests that hemoglobin does not require a refrigeration facility and/or apparatus that are necessary for other blood substitutes available in the market. The preservation and storage of the hemoglobin from the 'Befu' plant extracts are more broadly optimizable in temperature than those of other blood substitutes available publicly.

Figure 7A:
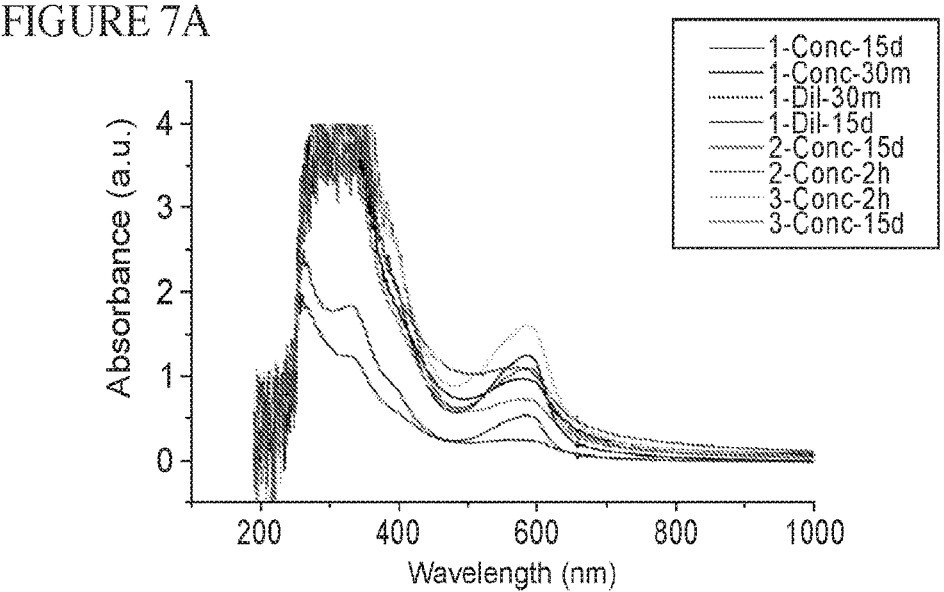
FIG. 7A illustrates presence of human hemoglobin using UV-VIS spectroscopy in diluted and concentrated samples kept for 2 hours and for 15 days.

Example 5—Detection of Hemoglobin and Other Blood Components from 'Befu' Plant Extracts Separately, ultraviolet-visible spectroscopy was performed using different samples to detect hemoglobin from 'Befu' plant extracts over 15 days. Spectra were collected using an Agilent model 8453 UV-VIS scanning spectrophotometer over a wavelength range from 200 to 800 nm. The samples were measured against water as reference. All samples were used as prepared and loaded into a quartz cell for measurements. FIG. 7A confirms that human hemoglobin is detected by UV-VIS spectroscopy in diluted and concentrated samples over the time, which shows characteristic absorption peaks of human hemoglobin as one clearly pronounced at 575 nm.

Figure 7B:
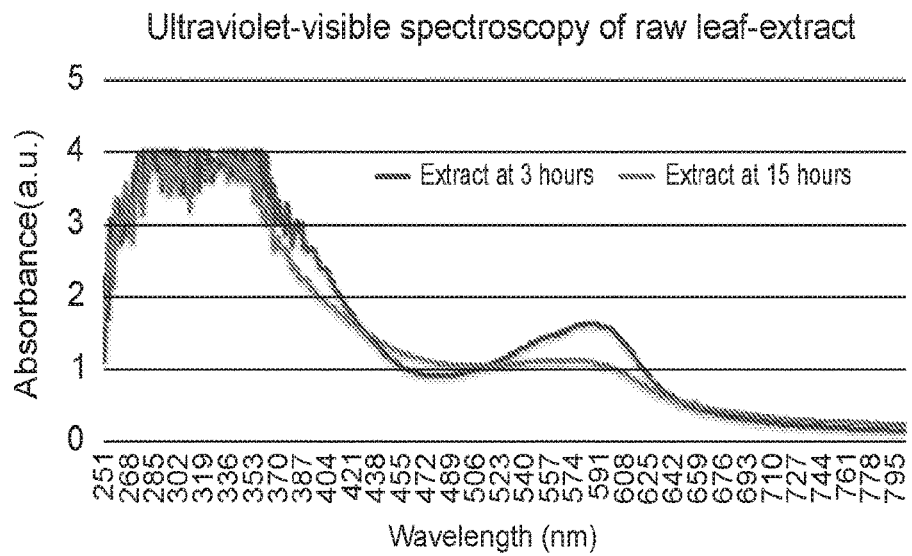
FIG. 7B shows presence of hemoglobin from 'Befu' leaf extract composition measured over time at 3 hours after producing a solution of the extract and 15 days after. Reduction in the hemoglobin peak at about 578 is observed over time consistent with expectations. Peaks at lower wavelengths indicate presence of other elements in this extract as confirmed by inductively coupled plasma mass spectrometry.
Figure 7C:
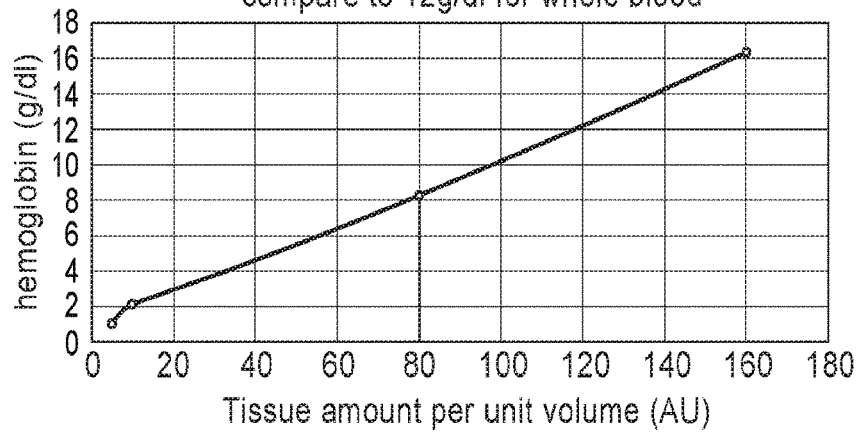
FIG. 7C shows high levels of hemoglobin following isolation and preservation of extract from 'Befu' plant using absorption wavelengths about at 575 nm.

The UV-VIS absorption spectra (FIG. 7B) of the 'Befu' leaf extract was consistent with the presence of hemoglobin with absorption peak around 575-578 nm. The height of the peak was observed to be lower for extract solutions analyzed after two weeks, suggesting a need for preservation methods of extracts maintained in liquid solution, as is the case with human blood.

To further examine the nature of the hemoglobin, samples were also sent for Western blot analysis by the Dana-Farber Cancer Institute core facility using samples from whole leaf extract. To assess hemoglobin, approximately 15 μg/lane of protein was loaded in 4-15% gradient polyacrylamide gel with Tris/Glycine running buffer system. Antibodies were used according to manufacturer recommended dilution (for 0/% sub unit 1:250 and for & sub unit 1:500 delusion) and Horseradish Peroxidase (HRP)-conjugated secondary antibody was used at 1:5000 dilutions. Antibodies used for western blot were from Abcam, for alpha subunit, ab82871 Rabbit polyclonal and for beta subunit, ab93825 Rabbit polyclonal. Gels were run for 33 minutes at 175 volts. Gels were transferred to Nitrocellulose membranes by semidry electrophoretic blotting at 12 volts for 60 minutes. Blots were developed using x-o-mat film and autoradiographs were scanned.

Western blot and ELISA analyses were conducted with the 'Befu' extract samples. FIG. 8A displays the concentration of hemoglobin in the sample. Western blot analysis also showed positive presence of human α-hemoglobin and weaker b-hemoglobin presence (FIGS. 8B and 8C). This observation appears consistent with the broad UV-Vis absorption peak which is near the characteristic wavelength of human α-hemoglobin.

Observed peaks at lower wavelengths by the UV-VIS absorption spectra suggest the presence of other elements in this extract. To perform ICP-MS on 'Befu' samples, 0.5 ml of the original samples (non lyophilized) were filtered, and raised to 10 ml with 2% nitric matrix. Standards were made with Ca, Mg, Na, and K at a range of 10 down to 0.001 pg/ml. All other elements were listed at a range of 1.0 down to 0.0001 μg/ml. The presence of these elements was corroborated with inductively coupled plasma mass spectrometry (ICP-MS) study of the extract, which revealed many essential mineral elements found in human blood. FIGS. 9A and 9B show a list of the essential mineral elements with concentration levels determined for a sample diluted to about 0.5 g/dl of hemoglobin. The combined presence of these elements with high levels of hemoglobin in the leaf of a plant is unusual, and suggest that there is a special need for 'blood' in the leaves of these plants. The function of such high levels of blood components may be indicated to be directed to the structure and stability of the hemoglobin.

Example 6—Abiotic Factors for Hemoglobin Gene Expression

In general, hemoglobin in plants may function in facilitating delivery of oxygen, transporting and buffering oxygen levels, and scavenging nitric oxide. The potential function or need of high level of blood components in the leaves of this species of *Justicia* plant can be caused by abiotic factors such as high temperatures combined with the dry season characteristic of some tropical regions. Regions with long arid or dry seasons and high temperatures can create significant abiotic stresses on plants. Under such conditions, species of evergreen perennials like *Justicia* may need to adapt to an increased need to close the stomata in their leaves, since open stomata expose the plant to the risk of losing the scarce water supply through transpiration. Open stomata are typically the route through which oxygen is released to the atmosphere during photosynthesis. Because of the increased need to close the stomata, a possible adaptation may mean increased expression of hemoglobin or 'blood' to help in oxygen storage and/or diffusion. This is consistent with the growing consensus that hemoglobin in some plants aids with oxygen storage or diffusion and that hemoglobin helps plants improve resistance to different biotic or abiotic stresses. Thus, Abiotic factors may influence hemoglobin gene expression at such high levels in the leaves.

Example 7—In Vitro Studies of 'Befu' Extracts on Cancer

To test whether high level of blood components in 'Befu' extract can impact on a sample of normal and cancer cell lines, clonogenic cell survival assay was conducted.

Primary human umbilical cord vein endothelium cells (HUVEC) were purchased from LONZA and was grown in a monolayer using Endothelial Cell Growth Medium with Bullet kit recommended by the company (LONZA). The cells were incubated at 37 Celsius with 5% CO2 under relative humidity. Trypsin from GIBCO were used to detach the cells and same amount of Trypsin Neutralizer (TN, GIBCO) was used to neutralize the Trypsin before adding the cell culture media.

Adenocarcinomic human alveolar basal epithelial cells (A549), PC3 human prostate cancer cell lines, and RWPE-1 *Homo sapiens* normal prostate epithelial cell line were purchased from ATCC and cultured in RPMI-1640 media supplemented with 10% FBS. Cells were incubated at 37° C. in a humidified atmosphere (5% CO2, 95% air). 500 cells per well were seeded in 6-well plates on day one. Cells were treated with different concentrations of 'Befu' and experiments performed in triplicates.

Clonogenic cell survival assay was done following normal protocol (16). Twenty four hours after treatment, all samples were reseeded as 104 cells per well in 6 well plates and was triplicated. Fourteen days after re-seeding colonies (>50 cells/colony) were fixed with 75% Ethanol and stained with 1% crystal violet (Sigma).

Figure 10A:
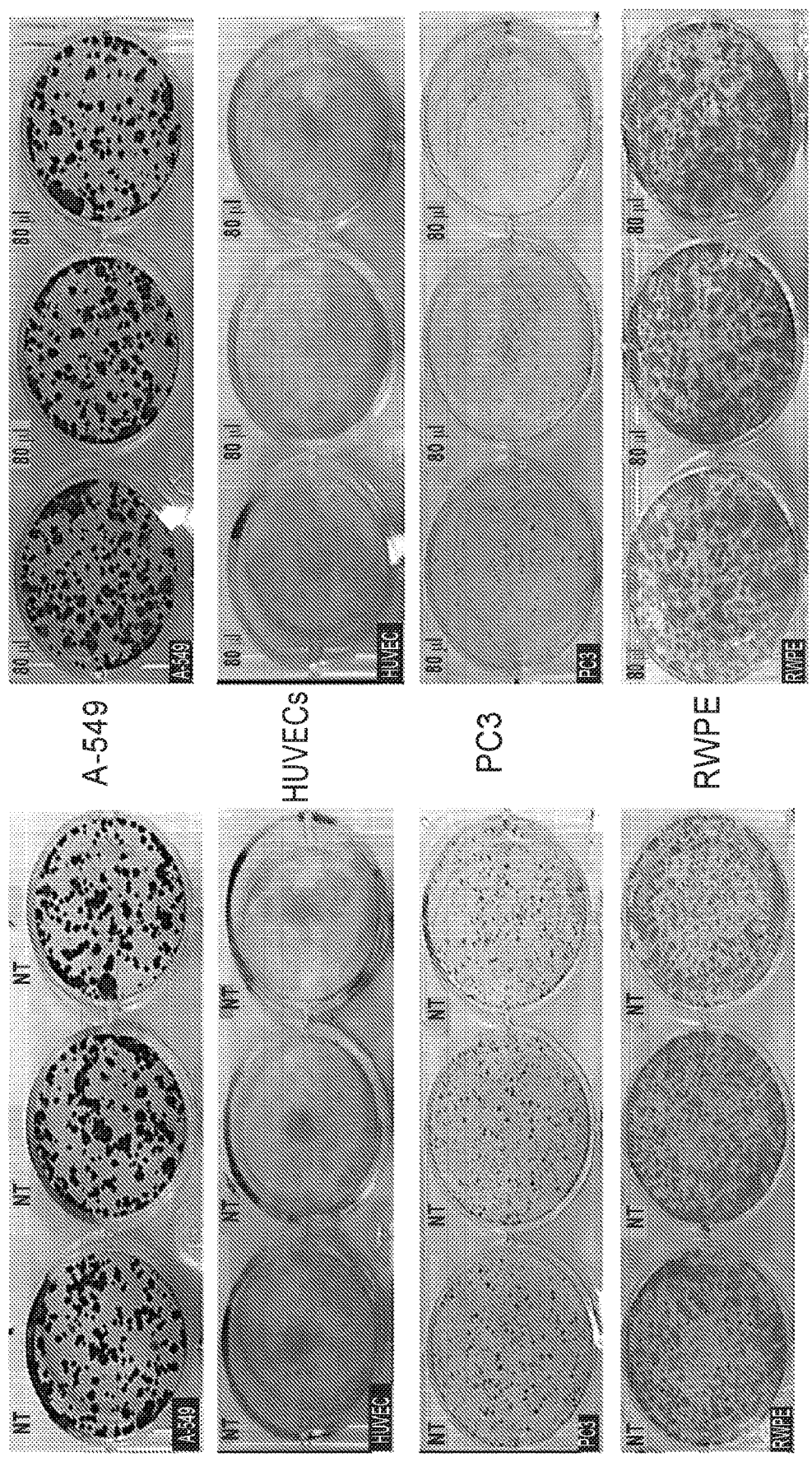
FIGS. 10A-10C shows clonogenic survival assay results showing the effect of 'Befu' extract on normal and cancer cells.
Figure 10B:
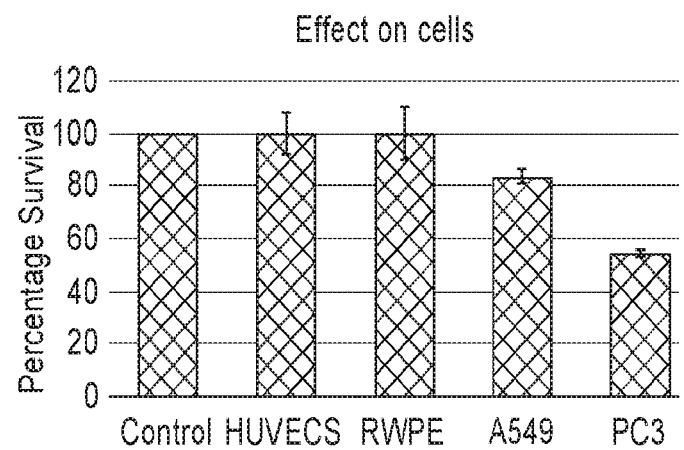

The results (FIGS. 10A and 10B) showed little effect of the leaf extract on normal cells: RWPE prostate cell lines and human umbilical vein endothelial cells. Interestingly same amounts of the extract showed an effect on PC-3 prostate cancer cells with clonogenic survival reducing to ca. 50%.

Example 8—In Vivo Studies of 'Befu' Extracts

In studies of renal responses to 'Befu' extract, C57B16J mice (Jackson Laboratory, Bar Harbor, Me.) were utilized. Mice were divided into two cohorts. Cohort A (n=4) mice were administered with the extract with hemoglobin at 180 mg/100 g body weight, as in previous studies assessing hemoglobin effect on kidney function. Cohort B mice served as control, with the sterile water used in hemoglobin extract administered via intraperitoneal injection. Mice were euthanized 24 hours after the injections. Blood from euthanized mice was analyzed (at VRL-LLC lab) for blood urea nitrogen (BUN) levels to evaluate any acute effect on kidney function. Non-euthanized mice were observed over three weeks.

Figure 10C:
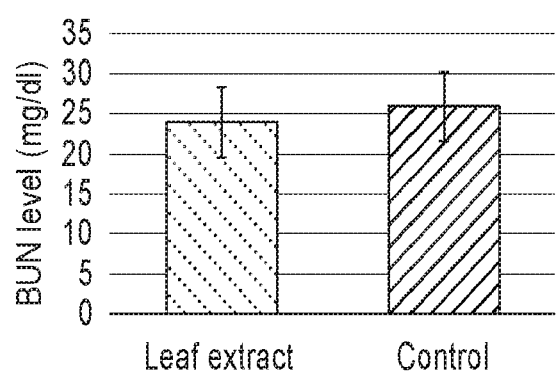

In-vivo studies indicated no acute effect of 'Befu' extract on kidney performance (FIG. 10C). Mice were administered with 200 µl of extract containing 18 g/dl hemoglobin concentration via intra-peritoneal injection. After 1 day, the mice were euthanized and blood urea nitrogen (BUN) levels analyzed. FIG. 10C shows comparable BUN levels for animals in mice administered with the extract and mice in control cohort administered with deionized water which was used to constitute the extract. All mice appeared healthy prior to being euthanized. A separate cohort of mice also administered with the extract was observed for over three weeks and remained as healthy as mice which were not administered with the extract.

Example 9—Morphological Properties *Justicia sanguinis* 'Befu' Plant

The following is a detailed description of the new *Justicia sanguinis* cultivar named 'Befu'. Data was collected in Orlando, Fla., U.S.A.

'Befu' is an herb which grows to about 40 inches in maximum height with leaves opposite. See FIG. 11B.

The plant is green with red rings present at the base of petiole. To date no flower structures have been observed on plants of 'Befu.'

Color determinations are in accordance with The Royal Horticultural Society Colour Chart 2001 edition, except where general color terms of ordinary dictionary significance are used. The growing requirements are similar to those typically used for this genus of plants. 'Befu' has not been tested under all possible conditions and phenotypic differences may be observed with variations in environmental, climatic, and cultural conditions, however, without any variance in genotype.

The botanical classification is proposed to be *Justicia sanguinis* 'Befu'.

Disease and pest resistance: Plants of the new cultivar have not been observed for disease and pest resistance.

The following traits in combination distinguish the *Justicia sanguinis* 'Befu' from a check variety *Justicia* Plant named 'ZEBRA'.

TABLE 1

*Justicia sanguinis* 'Befu' Plant Traits

| Characteristics | New Variety (Befu) | Check Variety (Zebra) |
|---|---|---|
| Plant growth habit | Upright | Upright |
| Plant propagation | Asexually propagated by stem cuttings and cloning | Terminal cuttings |
| Plant vigor | N/A | Medium |
| Height | Up to 101.6 cm | 23.2 cm |
| Leaf arrangement | Opposite | Opposite |
| Compound or single | Single | Single |
| Leaf shape | Acute, Lanceolate | Cordate |
| Leaf apex | Acuminate | Apiculate |
| Leaf base | Obtuse | Cordate |

TABLE 1-continued

*Justicia sanguinis* 'Befu' Plant Traits

| Characteristics | New Variety (Befu) | Check Variety (Zebra) |
|---|---|---|
| Leaf margin | Crenate | Entire |
| Venation pattern | Pinnate | Pinnate |
| Leaf attachment | Petiolate | Petiolate |
| Resistance to pests or diseases | Plants have not been observed for disease and pest resistance | Plants have not been observed for disease and pest resistance |
| Genetically-modified organism | NO | NO |
| Hemoglobin | High | N/A |

Example 10—Morphological Comparisons of *Justicia sanguinis* 'Befu' Plant with Other *Justicia* Species Applicant will conduct further morphological comparisons between the presently disclosed *Justicia sanguinis* species of plants, and other plants in the *Justicia* genus. The morphological features of the new species of *Justicia sanguinis* plant, named 'Befu' will be compared with one or more commonly known *Justicia* plant species selected from the group consisting of *Justicia Americana, Justicia brandegeeana, Justicia carnea, Justicia ovata, Justicia procumbens, Justicia pectoralis Jacq., Justicia gendarussa Buim. f, Justicia anselliana, Justicia adhatoda, Justicia secunda* and *Justicia pictifolia*.

A list of the various morphologies that will be compared between the various species includes, but is not limited to, botanical classification, plant life forms, plant growth habit, plant origin, plant propagation, height, width, vigor, time to initiate roots, time to produce a rooted cutting or linger, time to harvest, growth rate, root system, stem features (branching habit, average number of main stems, pinching, stem diameter, stem length, stem branch strength, stem color, stem shape, pubescence, internode length, aspect, strength), foliage features (texture, leaf arrangement, compound or single, quantity of leaves per stem, leaf shape, leaf apex, leaf base, leaf length, leaf width, pubescence, leaf margin, young leaf color (lower and upper surface), mature leaf color (lower and upper surface), vein color, venation pattern, leaf attachment, petiole dimensions, petiole color), flower features (inflorescence arrangement, flowering habit, quantity of flowers per stem, quantity of flower buds per stem, quantity of flowers and buds per plant, natural flowering season, fragrance, flower bud length, flower bud diameter, flower bud shape, bud color, rate of bud opening, flower aspect, flower shape, flower dimension, flower longevity, petal appearance, petal texture, number of petals, fused or unfused, petal appearance, petal shape, petal margin, petal apex, petal length, petal width, petal color), sepal features (number of sepal, sepal aspect, sepal shape, sepal margin sepal apex, sepal base, sepal surface, sepal dimensions, young sepal color, mature sepal color), calyx shape, calyx dimension, peduncle dimensions, peduncle aspect, peduncle color, peduncle strength, and reproductive organ features (stamen number, anther shape, anther dimensions, anther color, amount of pollen, pollen color, pistil number, pistil dimensions, stigma shape, stigma color, style length, style color, ovary color).

The cultivated 'Befu' cultivar will also be compared to other *Justicia* plants found near the cultivated space where the 'Befu' was identified. The morphological comparison will include a comparison of one or more of the features described in the preceding paragraph. It is expected that this data will further demonstrate the morphological differences between the presently disclosed *Justicia sanguinis* species, with other existing *Justicia* species.

Example 11—Comparisons of Extracts from *Justicia sanguinis* 'Befu' Plant with Extracts from Other *Justicia* Species Applicant has hereby described extracts and methods of producing the same, of a newly discovered *Justicia sanguinis* 'Befu' plant with unique properties and applications. Applicant has demonstrated through DNA and morphological analysis that the presently disclosed 'Befu' plant represents a previously unknown species of *Justicia*. In order to further distinguish the presently claimed extracts produced from *Justicia sanguinis* from those of other plants, Applicant will compare the claimed extracts with those produced from other *Justicia* species.

Extracts will be produced as described in earlier portions of this disclosure. Briefly, plant leaf tissue from each plant will be added to water at a temperature of 180° F. a water to leaf ratio of 1:1 to 30:1. The liquid portion of the extract will be removed and analyzed via ICP-MS. Extracts from *Justicia sanguinis* plant, named 'Befu' will be compared with the extracts from one or more commonly known *Justicia* plant species selected from the group consisting of *Justicia Americana, Justicia brandegeeana, Justicia carnea, Justicia ovata, Justicia procumbens, Justicia pectoralis Jacq., Justicia gendarussa Buim. f. Justicia anselliana, Justicia adhatoda, Justicia secunda* and *Justicia picifolia*.

Extracts form the cultivated 'Befu' cultivar will also be compared to extracts from other *Justicia* plants found near the cultivated space where the 'Befu' was identified. The morphological comparison will include a comparison of one or more of the features described in the preceding paragraph. It is expected that this data will further demonstrate the morphological differences between the presently disclosed *Justicia sanguinis* species, with other existing *Justicia* species.

DEPOSIT INFORMATION

A voucher specimen of 'Befu' has been deposited in the U.S. Herbarium (Smithsonian Institution). DNA barcode voucher sent by Wilfred F. Ngwa taken from a plant cultivation in Orlando, Fla., U.S.A. Dated: 19 Jun. 2017. Verification: W. J. Kress #17-8936 (USA).

In addition, a sample of the *Justicia sanguinis* 'Befu' stem cuttings (seeds) of this disclosure have been deposited with the American Type Culture Collection (ATCC®) Patent Depository located at 10801 University Boulevard, Manassas, Virginia 20110 on Aug. 13, 2021. The deposit was made under ATCC Accession No. PTA-127079.

To satisfy the enablement requirements of 35 U.S.C. 112, and to certify that the deposit of the isolated strain of the present disclosure meets the criteria set forth in 37 C.F.R. 1.801-1.809, Applicants hereby make the following statements regarding the deposited 'Befu' (deposited as ATCC Accession No. PTA-127079.

1. During the pendency of this application, access to the disclosure will be afforded to the Commissioner upon request;
2. All restrictions on availability to the public will be irrevocably removed upon granting of the patent under conditions specified in 37 CFR 1.808;
3. The deposit will be maintained in a public repository for a period of 30 years or 5 years after the last request or for the effective life of the patent, whichever is longer;
4. A test of the viability of the biological material at the time of deposit will be conducted by the public depository under 37 C.F.R. 1.807; and
5. The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of plant cuttings of the same variety with ATCC Accession No. PTA-127079.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as an acknowledgment or any form of suggestion that they constitute valid prior art or form part of the common general knowledge in any country in the world.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the non-limiting exemplary methods and materials are described herein.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Nothing herein is to be construed as an admission that the present invention is not entitled to antedate such publication by virtue of prior invention.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

FURTHER EMBODIMENTS OF THE INVENTION

Other subject matter contemplated by the present disclosure is set out in the following numbered embodiments:

1. A method for treating prostate cancer, said method comprising administering an extract from a *Justicia sanguinis* plant to a patient in need thereof, thereby reducing the survival of prostate cancer cells in said patient.

1.1 A method for treating prostate cancer, said method comprising administering an extract from a *Justicia sanguinis* plant to a patient in need thereof, thereby reducing the survival of prostate cancer cells in said patient; wherein a representative sample of seed or tissue culture of said *Justicia sanguinis* plant has been deposited under ATCC Accession No. PTA-127079.

2. The method of embodiment 1 or 1.1, wherein the extract is produced by contacting the *Justicia sanguinis* plant or part thereof with a solvent, thereby creating an extraction solution; and recovering the liquid phase of the extraction solution, thereby producing the extract.

3. The method of embodiment 2, wherein the solvent is water.

4. The method of embodiment 3, wherein the water is at a temperature between about 60° F. and about 180° F. at the time that the solvent is contacted with the plant.

5. The method of embodiment 3, wherein the water is maintained at a temperature between about 60° F. and about 180° F. until the liquid phase is recovered to produce the extract.

6. A method for reducing survival rate of prostate cancer cells in vitro, said method comprising contacting prostate cancer cells with an extract from a *Justicia sanguinis* plant, thereby reducing the survival rate of the prostate cancer cells compared with control prostate cancer cells that are not contacted with the extract.

6.1 A method for reducing survival rate of prostate cancer cells in vitro, said method comprising contacting prostate cancer cells with an extract from a *Justicia sanguinis* plant, thereby reducing the survival rate of the prostate cancer cells compared with control prostate cancer cells that are not contacted with the extract; wherein a representative sample of seed or tissue culture of said *Justicia sanguinis* plant has been deposited under ATCC Accession No. PTA-127079.

7. The method of embodiment 6 or 6.1, wherein the extract is produced by contacting the *Justicia sanguinis* plant or part thereof with a solvent, thereby creating an extraction solution; and recovering the liquid phase of the extraction solution, thereby producing the extract.

8. The method of embodiment 7, wherein the solvent is water.

9. The method of embodiment 8, wherein the water is at a temperature between about 60° F. and about 180° F. at the time that the solvent is contacted with the plant.

10. The method of embodiment 8, wherein the water is maintained at a temperature between about 60° F. and about 180° F. until the liquid phase is recovered to produce the extract.

11. A method for producing a shelf-stable blood substitute, said method comprising the steps of:
 a) contacting a *Justicia sanguinis* plant or part thereof with a solvent; thereby creating an extraction solution,
 b) recovering the liquid phase of the extraction solution,
 c) lyophilizing the liquid phase to produce a dry, shelf-stable blood substitute.

11.1 A method for producing a shelf-stable blood substitute, said method comprising the steps of:
 a) contacting a *Justicia sanguinis* plant or part thereof with a solvent; thereby creating an extraction solution,
 b) recovering the liquid phase of the extraction solution,
 c) lyophilizing the liquid phase to produce a dry, shelf-stable blood substitute;
wherein a representative sample of seed or tissue culture of said *Justicia sanguinis* plant has been deposited under ATCC Accession No. PTA-127079.

12. The method of embodiment 11 or 11.1, wherein the shelf-stable blood substitute retains at least 50% of its hemoglobin content for two weeks at room temperature.

13 The method of embodiment 11, wherein the shelf-stable blood substitute retains at least 60% of its hemoglobin content for two weeks at room temperature.

14 The method of embodiment 11, wherein the shelf-stable blood substitute retains at least 70%0 of its hemoglobin content for two weeks at room temperature.

15 The method of embodiment 11, wherein the shelf-stable blood substitute retains at least 80% of its hemoglobin content for two weeks at room temperature.

16. The method of embodiment 11, wherein the water is at a temperature between about 60° F. and about 180° F. at the time that the solvent is contacted with the plant.

17. The method of embodiment 11, wherein the water is maintained at a temperature between about 60° F. and about 180° F. until the liquid phase is recovered from the extraction solution.

18. The method of any one of embodiments 11-17, wherein the lyophilization of step c) occurs at −50° C. for 3 hours with a cooling rate of 1° C./minute; with primary drying at −50° C. for 60 hours at 3 Pa; and secondary drying at 0° C. for 4 hours and 20° C. for 8 hours at 3 Pa.

19. A method for producing a plant hemoglobin food additive, said method comprising the steps of:
 a) extracting plant hemoglobin by contacting a *Justicia sanguinis* plant or part thereof with a solvent; thereby creating an extraction solution, and
 b) recovering the liquid phase of the extraction solution, thereby producing the hemoglobin food additive.

19.1 A method for producing a plant hemoglobin food additive, said method comprising the steps of:
 a) extracting plant hemoglobin by contacting a *Justicia sanguinis* plant or part thereof with a solvent, thereby creating an extraction solution, and
 b) recovering the liquid phase of the extraction solution, thereby producing the hemoglobin food additive;
wherein a representative sample of seed or tissue culture of said *Justicia sanguinis* plant has been deposited under ATCC Accession No. PTA-127079.

20. The method of embodiment 19 or 19.1, wherein the food additive is added to a meat substitute food product comprising wheat gluten.

21. The method of any one of embodiments 19, 19.1, or 20, wherein the solvent is water.

22. The method of embodiment 21, wherein the water is at a temperature between about 60° F. and about 180° F. at the time that step (a) begins.

23. The method of embodiment 21, wherein the water is maintained at a temperature between about 60° F. and about 180° F. until step (b).

24. The method of any one of embodiments 19-23, comprising the step of c) concentrating the food additive through centrifugation and/or lyophilization.

25. The method of embodiment 24, wherein the food additive is centrifuged at a sufficient speed and time to produce a pellet comprising plant hemoglobin.
26. The method of embodiment 25, wherein the food additive is centrifuged between about 4,000 rpm and 16,000 rpm.
27. The method of embodiment 25 or 26, wherein the food additive is centrifuged for between 2 minutes, and 5 hours.
28. The method of any one of embodiments 19-27, wherein a representative sample of seed or tissue culture of said *Justicia sanguinis* plant has been deposited under ATCC Accession No. PTA-127079.
29. The method of any one of embodiments 19-28, wherein the hemoglobin food additive is added to a primary flavor precursor compound selected from the group consisting of glucose, ribose, fructose, lactose, xylose, arabinose, glucose-6-phosphate, maltose, and galactose, and mixtures of two or more thereof and/or a secondary flavor precursor compound selected from the group consisting of cysteine, cystine, selenocysteine, thiamine, methionine, and mixtures of two or more thereof.
30. A composition comprising:
  a) an extract from a *Justicia sanguinis* plant or plant part thereof, said extract comprising plant hemoglobin.
30.1 A composition comprising:
  a) an extract from a *Justicia sanguinis* plant or plant part thereof, said extract comprising plant hemoglobin;
wherein a representative sample of seed or tissue culture of said *Justicia sanguinis* plant has been deposited under ATCC Accession No. PTA-127079.
31. The composition of embodiment 30 or 30.1, wherein the extract has been treated by a human cytochrome $b_5$ to convert methemoglobin in the extract to oxy-hemoglobin.
32. The composition of embodiment 30 or 30.1, wherein the extract comprises: b) human cytochrome $b_5$.
33. The composition of any one of embodiments 30-32 wherein the extract comprises one or more exogenously added blood analytes selected from the group consisting of Zn, Sn, O, Ni, Hg, Cd, Cu, Ti, V, and Sc.
34. A shelf-stable lyophilized extract from a *Justicia sanguinis* plant or plant part thereof.
34.1 A shelf-stable lyophilized extract from a *Justicia sanguinis* plant or plant part thereof; wherein a representative sample of seed or tissue culture of said *Justicia sanguinis* plant has been deposited under ATCC Accession No. PTA-127079.
35. The shelf-stable lyophilized extract of embodiment 34 or 34.1, wherein the extract comprises hemoglobin.
35.1 The shelf-stable lyophilized extract of embodiment 34 or 34.1, wherein said isolated hemoglobin comprises α-hemoglobin and β-hemoglobin.
36. The shelf-stable lyophilized extract of embodiment 35 or 35.1, wherein said extract retains at least 50% of its hemoglobin content for two weeks at room temperature.
37. The shelf-stable lyophilized extract of embodiment 35 or 35.1, wherein said extract retains at least 60% of its hemoglobin content for two weeks at room temperature.
38. The shelf-stable lyophilized extract of embodiment 35 or 35.1, wherein said extract retains at least 70% of its hemoglobin content for two weeks at room temperature.
39 The shelf-stable lyophilized extract of embodiment 35 or 35.1, wherein said extract retains at least 80% of its hemoglobin content for two weeks at room temperature.
39.1 The shelf-stable lyophilized extract of any one of embodiments 34-39, wherein said extract is a dietary supplement.
40. The shelf-stable lyophilized extract of any one of embodiments 34-39, wherein said extract is a blood substitute.
41. The shelf-stable lyophilized extract of any one of embodiments 34-39, wherein said extract is capable of treating a blood disorder, blood cancer and cancer.
42. The shelf-stable lyophilized extract of embodiment 41, wherein the blood disorder being treated is selected from the group consisting of anemia, hemophilia, and blood clots.
43. The shelf-stable lyophilized extract of embodiment 41, wherein the blood cancer being treated is selected from the group consisting of multiple myeloma, an acute leukemia, an advance phase chronic myelogenous leukemia (CML), a high risk myelodysplastic syndrome (MDS), an advanced myelofibrosis (MF), and a relapsed or refractory chronic lymphocytic leukemia (CLL).
44. A method for treating a patient with iron deficiency anaemia, said method comprising administering an extract from a *Justicia sanguinis* plant to a patient in need thereof, wherein said extract contains iron.
44.1 A method for treating a patient with iron deficiency anaemia, said method comprising administering an extract from a *Justicia sanguinis* plant to a patient in need thereof, wherein said extract contains iron; wherein a representative sample of seed or tissue culture of said *Justicia sanguinis* plant has been deposited under ATCC Accession No. PTA-127079.
45. The method of embodiment 44 or 44.1, wherein the extract is produced by contacting the *Justicia sanguinis* plant or part thereof with a solvent, thereby creating an extraction solution; and recovering the liquid phase of the extraction solution, thereby producing the extract.
46. The method of embodiment 45, wherein the solvent is water.
47. The method of embodiment 46, wherein the water is at a temperature between about 60° F. and about 180° F. at the time that the solvent is contacted with the plant.
48. The method of embodiment 46, wherein the water is maintained at a temperature between about 60° F. and about 180° F. until the liquid phase is recovered to produce the extract.

REFERENCES CITED

1. C. A. Appleby, J. D. Tjepkema, M. J. Trinick, Hemoglobin in a nonleguminous plant, *parasponia*: possible genetic origin and function in nitrogen fixation. *Science.* 220, 951-953 (1983).
2. C. R. Andersson, E. O. Jensen, D. J. Llewellyn, E. S. Dennis, A. W. J. Peacock, A new hemoglobin gene from soybean: A role for hemoglobin in all plants (nonsymbiotic/leghemoglobin/evolution). Plant Biol. 93, 5682-5687 (1996).
3. R. a Watts et al., A hemoglobin from plants homologous to truncated hemoglobins of microorganisms. *Proc. Natl. Acad. Sci. U.S.A.* 98, 10119-24 (2001).
4. X. Wang, M. S. Hargrove, Nitric oxide in plants: The roles of ascorbate and hemoglobin. *PLoS One.* 8 (2013), doi: 10.1371/journal.pone.0082611.
5. S. Jokipii-Lukkari, A. D. Frey, P. T. Kallio, H. Haggman, Intrinsic non-symbiotic and truncated haemoglobins and heterologous *Vitreoscilla* haemoglobin expression in plants. *J. Exp. Bot.* 60 (2009), pp. 409-422.
6. D. Bogusz et al., Functioning haemoglobin genes in non-nodulating plants. *Nature.* 331, 178-180 (1988).

7. K. J. Gupta, K. H. Hebelstrup, L. A. J. Mur, A. U. Igamberdiev, Plant hemoglobins: Important players at the crossroads between oxygen and nitric oxide. *FEBS Lett.* 585 (2011), pp. 3843-3849.
8. J. A. Hoy, M. S. Hargrove, The structure and function of plant hemoglobins. *Plant Physiol. Biochem.* 46 (2008), pp. 371-379.
9. G. M. Corrêa, A. F. C. de Alcintara, Chemical constituents and biological activities of species of *justicia*—a review. *Brazilian J. Pharmacogn.* 22 (2011), pp. 220-238.
10. M. B. Strader et al., Oxidative instability of hemoglobin E (β26 Glu→Lys) is increased in the presence of free a subunits and reversed by α-hemoglobin stabilizing protein (AHSP): Relevance to HbE/β-thalassemia. *Redox Biol.* 8, 363-374 (2016).
11. J. M. Harrington, D. J. Young, A. S. Essader, S. J. Sumner, K. E. Levine, Analysis of human serum and whole blood for mineral content by ICP-MS and ICP-OES: Development of a mineralomics method. *Biol. Trace Elem. Res.* 160, 132-142 (2014).
12. S. Kakar, F. G. Hoffman, J. F. Storz, M. Fabian, M. S. Hargrove, Structure and reactivity of hexacoordinate hemoglobins. *Biophys. Chem.* 152 (2010), pp. 1-14.
13. W. J. Kress et al., Plant DNA barcodes and a community phylogeny of a tropical forest dynamics plot in Panama. *Proc. Natl. Acad. Sci. U.S.A.* 106, 18621-6 (2009).
14. W. J. Kress et al., Advances in the use of DNA barcodes to build a community phylogeny for tropical trees in a Puerto Rican forest dynamics plot. *PLoS One.* 5 (2010), doi:10. 1371/journal.pone.0015409.
15. W. J. Kress, D. L. Erickson, *DNA Barcodes. Methods and Protocols* (2012; http://books.google.com/books?id=Ku2wPAAACAAJ %5Cnhttp://link.springer.com/10.10 07/978-1-62703-239-1_1%5Cnhttp://link.springer.com/10.1007/978-1-61779-591-6), vol. 858.
16. A. Munshi, M. Hobbs, R. E. Meyn, Clonogenic cell survival assay. *Methods Mol. Med.* 110, 21-28 (2005).
17. K. a Nath et al., Age sensitizes the kidney to heme protein-induced acute kidney injury. *Am. J. Physiol. Renal Physiol.* 304, F317-25 (2013).

What is claimed is:

1. A method for producing a shelf-stable blood substitute, said method comprising the steps of:
    a) contacting a *Justicia sanguinis* plant or part thereof with a solvent; thereby creating an extraction solution,
    b) recovering the liquid phase of the extraction solution,
    c) lyophilizing the liquid phase to produce a dry, shelf-stable blood substitute.
2. The method of claim 1, wherein the shelf-stable blood substitute retains at least 50% of its hemoglobin content for two weeks at room temperature.
3. The method of claim 1, wherein the shelf-stable blood substitute retains at least 60% of its hemoglobin content for two weeks at room temperature.
4. The method of claim 1, wherein the shelf-stable blood substitute retains at least 70% of its hemoglobin content for two weeks at room temperature.
5. The method of claim 1, wherein the shelf-stable blood substitute retains at least 80% of its hemoglobin content for two weeks at room temperature.
6. The method of claim 1, wherein the solvent is at a temperature between about 60° F. and about 180° F. at the time that the solvent is contacted with the plant.
7. The method of claim 1, wherein the solvent is maintained at a temperature between about 60° F. and about 180° F. until the liquid phase is recovered from the extraction solution.
8. The method of claim 1, wherein the lyophilization of step c) occurs at −50° C. for 3 hours with a cooling rate of 1° C./minute; with primary drying at −50° C. for 60 hours at 3 Pa; and secondary drying at 0° C. for 4 hours and 20° C. for 8 hours at 3 Pa.
9. The method of claim 6 or 7, wherein the solvent comprises water.

\* \* \* \* \*